US009226933B2

(12) United States Patent
Ritter

(10) Patent No.: US 9,226,933 B2
(45) Date of Patent: Jan. 5, 2016

(54) METHODS AND COMPOSITIONS FOR TREATING LACTOSE INTOLERANCE

(75) Inventor: Andrew J. Ritter, Los Angeles, CA (US)

(73) Assignee: Ritter Pharmaceuticals, Inc., Los Angeles, CA (US)

( * ) Notice: Subject to any disclaimer, the term of this patent is extended or adjusted under 35 U.S.C. 154(b) by 0 days.

(21) Appl. No.: 12/055,936

(22) Filed: Mar. 26, 2008

(65) Prior Publication Data
US 2008/0233092 A1 Sep. 25, 2008

Related U.S. Application Data

(63) Continuation of application No. 11/632,289, filed as application No. PCT/CT2005/026095 on Jul. 22, 2005, which is a continuation-in-part of application No. 10/710,588, filed on Jul. 22, 2004, now abandoned.

(51) Int. Cl.
A61K 35/747 (2015.01)
A61K 31/7016 (2006.01)
A23L 1/236 (2006.01)
A23L 1/30 (2006.01)
A23L 1/308 (2006.01)
G06Q 30/02 (2012.01)

(52) U.S. Cl.
CPC ........... *A61K 31/7016* (2013.01); *A23L 1/2363* (2013.01); *A23L 1/3014* (2013.01); *A23L 1/3081* (2013.01); *A61K 35/747* (2013.01); *G06Q 30/0212* (2013.01)

(58) Field of Classification Search
CPC ........... A23V 2002/00; A23V 2200/32; A23V 2200/12; A23V 2250/5118; A23V 2250/64; A23V 2250/642; A23V 2300/34; A61K 2300/00; A61K 33/10; A61K 33/14; A61K 31/192; A61K 31/7016; A61K 31/715; A61K 35/74; A61K 38/47; A61K 31/702; A61K 35/747; A61K 35/742; A61K 35/744; A61K 35/745; A61K 31/155; A61K 38/26; A61K 38/28; A61K 38/465; A61K 45/06; A61K 9/4825
See application file for complete search history.

(56) References Cited

U.S. PATENT DOCUMENTS

| | | |
|---|---|---|
| 3,048,526 A | 8/1962 | Boswell |
| 3,108,046 A | 10/1963 | Harbit et al. |
| 3,536,809 A | 10/1970 | Appleweig |
| 3,598,123 A | 8/1971 | Zaffaroni |
| 3,627,583 A | 12/1971 | Troy et al. |
| 3,718,739 A | 2/1973 | Cayle |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,478,822 A | 10/1984 | Haslam et al. |
| 4,532,126 A | 7/1985 | Ebert et al. |
| 4,625,494 A | 12/1986 | Iwatschenko et al. |
| 4,629,694 A | 12/1986 | Harpel |
| 4,656,066 A | 4/1987 | Wittwer |
| 4,671,953 A | 6/1987 | Stanley et al. |
| 4,786,505 A | 11/1988 | Lovgren et al. |
| 4,800,083 A | 1/1989 | Hom et al. |
| 4,806,368 A | 2/1989 | Reddy |
| 4,888,171 A | 12/1989 | Okonogi et al. |
| 4,904,479 A | 2/1990 | Illum |
| 4,919,939 A | 4/1990 | Baker |
| 4,935,243 A | 6/1990 | Borkan et al. |
| 4,944,952 A | 7/1990 | Kobayashi et al. |
| 4,950,484 A | 8/1990 | Olthoff et al. |
| 4,957,763 A | 9/1990 | Saita et al. |
| 4,959,234 A * | 9/1990 | Ahmed et al. ................ 426/580 |
| 4,987,150 A | 1/1991 | Kurono et al. |
| 5,013,726 A | 5/1991 | Ivy et al. |
| 5,032,509 A | 7/1991 | Matsumoto et al. |
| 5,059,595 A | 10/1991 | Le Grazie |
| 5,073,543 A | 12/1991 | Marshall et al. |
| 5,118,521 A | 6/1992 | Sonoike et al. |
| 5,120,548 A | 6/1992 | McClelland et al. |
| 5,139,575 A | 8/1992 | Matsuda et al. |
| 5,149,640 A | 9/1992 | Onishi et al. |
| 5,219,842 A | 6/1993 | Okada et al. |
| 5,225,202 A | 7/1993 | Hodges et al. |
| 5,294,546 A | 3/1994 | Dombou et al. |

(Continued)

FOREIGN PATENT DOCUMENTS

| | | |
|---|---|---|
| AU | 624590 B2 | 6/1989 |
| AU | 2006257751 B2 | 12/2006 |

(Continued)

OTHER PUBLICATIONS

DFO-Nutrition Services: Spotlight for Sep. 1995. Lactose Intolerance: Common Concerns. Available at http://www.milk.org/spotsept.htm. Accessed May 17, 1999.

Gilat, et al. Lactase in man: a nonadaptable enzyme. Gastroenterology. Jun. 1972;62(6):1125-7.

Hertzler, et al. Colonic adaptation to daily lactose feeding in lactose maldigesters reduces lactose intolerance. Am J Clin Nutr. Aug. 1996;64(2):232-6.

Kim, et al. Lactobacillus acidophilus as a dietary adjunct for milk to aid lactose digestion in humans. J Dairy Sci. 1983; 66(5):959-66.

Kretchmer, N. Lactose and lactase—a historical perspective. Gastroenterology. Dec. 1971;61(6):805-13.

(Continued)

Primary Examiner — Debbie K Ware
(74) Attorney, Agent, or Firm — Knobbe Martens Olson & Bear LLP

(57) ABSTRACT

The invention provides methods and compositions for treating lactose intolerance. In embodiments, the invention provides methods and composition for decreasing symptoms of lactose intolerance by administering to an individual suffering from lactose intolerance increasing doses of lactose using a protocol such that at the end of treatment the individual's symptoms of lactose intolerance are decreased and such that symptoms remain decreased after a period of time.

15 Claims, No Drawings

(56) References Cited

U.S. PATENT DOCUMENTS

| | | | |
|---|---|---|---|
| 5,354,556 A | 10/1994 | Sparks et al. | |
| 5,378,833 A | 1/1995 | Katta et al. | |
| 5,439,893 A | 8/1995 | Richards et al. | |
| 5,466,472 A | 11/1995 | Kuma et al. | |
| 5,550,106 A | 8/1996 | Petschow et al. | |
| 5,591,767 A | 1/1997 | Mohr et al. | |
| 5,610,184 A | 3/1997 | Shahinian, Jr. | |
| 5,623,071 A | 4/1997 | Kitahata et al. | |
| 5,639,476 A | 6/1997 | Oshlack et al. | |
| 5,641,759 A | 6/1997 | Patterson et al. | |
| 5,644,012 A | 7/1997 | Iritani et al. | |
| 5,674,533 A | 10/1997 | Santus et al. | |
| 5,709,857 A | 1/1998 | Morelli et al. | |
| 5,716,615 A | 2/1998 | Cavaliere Vesely et al. | |
| 5,733,556 A | 3/1998 | Schrier et al. | |
| 5,733,575 A | 3/1998 | Mehra et al. | |
| 5,744,134 A | 4/1998 | Paul | |
| 5,827,526 A | 10/1998 | Dohnalek et al. | |
| 5,837,284 A | 11/1998 | Mehta et al. | |
| 5,840,860 A | 11/1998 | Annison et al. | |
| 5,861,289 A | 1/1999 | Nakayama et al. | |
| 5,871,776 A | 2/1999 | Mehta | |
| 5,895,648 A | 4/1999 | Cavaliere Vesely et al. | |
| 5,902,632 A | 5/1999 | Mehta | |
| 5,906,982 A | 5/1999 | Prieto et al. | |
| 5,952,021 A | 9/1999 | Santus | |
| 5,952,205 A | 9/1999 | Catani et al. | |
| 5,962,275 A | 10/1999 | Horsch et al. | |
| 6,093,425 A | 7/2000 | Kamarei | |
| 6,139,875 A | 10/2000 | Adams et al. | |
| 6,197,758 B1 | 3/2001 | Ohtsuki et al. | |
| 6,221,350 B1 | 4/2001 | Brown et al. | |
| 6,241,983 B1 | 6/2001 | Paul et al. | |
| 6,258,380 B1 | 7/2001 | Overholt | |
| 6,368,641 B1 * | 4/2002 | Khatchatrian et al. | 426/46 |
| 6,399,124 B1 | 6/2002 | Lesens et al. | |
| 6,420,473 B1 | 7/2002 | Chittamuru et al. | |
| 6,423,833 B1 | 7/2002 | Catani et al. | |
| 6,451,584 B2 | 9/2002 | Tomita et al. | |
| 6,455,052 B1 | 9/2002 | Marcussen et al. | |
| 6,461,607 B1 | 10/2002 | Farmer | |
| 6,468,525 B1 | 10/2002 | Watson et al. | |
| 6,471,999 B2 * | 10/2002 | Couzy et al. | 426/2 |
| 6,482,435 B1 | 11/2002 | Stratton et al. | |
| 6,544,568 B2 | 4/2003 | La Droitte et al. | |
| 6,569,457 B2 | 5/2003 | Ullah et al. | |
| 6,572,871 B1 | 6/2003 | Church et al. | |
| 6,576,251 B1 | 6/2003 | Stahl et al. | |
| 6,599,882 B1 | 7/2003 | Rogoff et al. | |
| 6,706,287 B2 * | 3/2004 | Ranganathan et al. | 424/490 |
| 6,750,331 B1 | 6/2004 | Takaichi et al. | |
| 6,783,780 B1 | 8/2004 | De Jong et al. | |
| 6,797,266 B2 | 9/2004 | Naidu | |
| 6,833,260 B1 * | 12/2004 | Ruch | 435/207 |
| 6,835,376 B1 | 12/2004 | Neeser et al. | |
| 6,841,181 B2 | 1/2005 | Jager et al. | |
| 6,863,918 B2 | 3/2005 | Bindels et al. | |
| 6,884,445 B2 | 4/2005 | Navarro et al. | |
| 6,929,793 B2 | 8/2005 | Spivey-Krobath et al. | |
| 6,936,598 B2 | 8/2005 | Khoo et al. | |
| 6,960,341 B2 | 11/2005 | Viscomi et al. | |
| 6,989,166 B2 | 1/2006 | Te et al. | |
| 7,029,702 B2 | 4/2006 | Ritter | |
| 7,101,553 B2 | 9/2006 | Haschke et al. | |
| 7,101,565 B2 | 9/2006 | Monte | |
| 7,166,451 B1 | 1/2007 | Yang et al. | |
| 7,172,777 B2 | 2/2007 | Schmitt et al. | |
| 7,195,906 B2 | 3/2007 | Collins et al. | |
| 7,214,370 B2 | 5/2007 | Naidu | |
| 7,422,764 B2 | 9/2008 | Navarro et al. | |
| 7,435,431 B2 | 10/2008 | Johnson | |
| 7,491,518 B2 | 2/2009 | Okada et al. | |
| 7,879,363 B2 | 2/2011 | Ritter | |
| 8,486,668 B2 | 7/2013 | Ritter et al. | |
| 8,492,124 B2 | 7/2013 | Ritter et al. | |
| 2002/0034496 A1 | 3/2002 | Ritter | |
| 2003/0040492 A1 | 2/2003 | Haschke et al. | |
| 2003/0147995 A1 | 8/2003 | Koss et al. | |
| 2004/0005305 A1 | 1/2004 | Spivey-Krobath et al. | |
| 2004/0057943 A1 * | 3/2004 | Xaus Pey et al. | 424/93.45 |
| 2004/0131659 A1 | 7/2004 | Gibson et al. | |
| 2004/0161422 A1 | 8/2004 | Ranganathan | |
| 2004/0213828 A1 | 10/2004 | Smith | |
| 2004/0219157 A1 | 11/2004 | Rochat et al. | |
| 2005/0074442 A1 | 4/2005 | Ranganathan | |
| 2005/0079244 A1 | 4/2005 | Giffard et al. | |
| 2005/0119222 A1 | 6/2005 | Norton et al. | |
| 2005/0147710 A1 | 7/2005 | Teckoe et al. | |
| 2005/0164340 A1 | 7/2005 | Schlothauer et al. | |
| 2005/0180962 A1 * | 8/2005 | Raz et al. | 424/93.45 |
| 2005/0288250 A1 | 12/2005 | Rautonen et al. | |
| 2006/0008574 A1 | 1/2006 | Begli et al. | |
| 2006/0034993 A1 | 2/2006 | Saelzer | |
| 2006/0040001 A1 | 2/2006 | Johnson | |
| 2006/0093592 A1 | 5/2006 | Cheruvanky et al. | |
| 2006/0104965 A1 | 5/2006 | Ritter | |
| 2006/0141097 A1 | 6/2006 | Guo | |
| 2006/0165670 A1 | 7/2006 | Beer et al. | |
| 2006/0182727 A1 | 8/2006 | Yamashira et al. | |
| 2006/0234980 A1 | 10/2006 | Hashimoto et al. | |
| 2006/0246179 A1 | 11/2006 | Ammann et al. | |
| 2006/0287276 A1 | 12/2006 | Rhoades et al. | |
| 2007/0098762 A1 | 5/2007 | Stahl et al. | |
| 2007/0104700 A1 | 5/2007 | Garcia-Rodenas et al. | |
| 2007/0134391 A1 | 6/2007 | Prakash et al. | |
| 2007/0196439 A1 | 8/2007 | Catani et al. | |
| 2007/0196890 A1 | 8/2007 | Vulevic et al. | |
| 2007/0207132 A1 | 9/2007 | Speelmans et al. | |
| 2007/0248649 A1 | 10/2007 | Sawatzki et al. | |
| 2007/0274955 A1 | 11/2007 | Gibson et al. | |
| 2007/0274983 A1 | 11/2007 | Kluijtmans et al. | |
| 2008/0031814 A1 | 2/2008 | Hageman et al. | |
| 2008/0044493 A1 | 2/2008 | Sato et al. | |
| 2008/0064657 A1 | 3/2008 | Day et al. | |
| 2008/0108548 A1 | 5/2008 | Luyer et al. | |
| 2008/0112941 A1 | 5/2008 | Ritter | |
| 2008/0112942 A1 | 5/2008 | Farmer et al. | |
| 2008/0124323 A1 | 5/2008 | Boehm et al. | |
| 2008/0126195 A1 | 5/2008 | Ritter | |
| 2008/0171720 A1 | 7/2008 | Garssen et al. | |
| 2008/0193406 A1 | 8/2008 | Rull Prous et al. | |
| 2008/0193485 A1 | 8/2008 | Gorbach et al. | |
| 2008/0193627 A1 | 8/2008 | Van Eert et al. | |
| 2008/0199444 A1 | 8/2008 | Cui | |
| 2008/0207559 A1 | 8/2008 | Sawatzki et al. | |
| 2008/0213341 A1 | 9/2008 | Haji et al. | |
| 2008/0233092 A1 | 9/2008 | Ritter | |
| 2008/0260893 A1 | 10/2008 | Giffard et al. | |
| 2008/0261916 A1 | 10/2008 | Jaszberenyi et al. | |
| 2008/0280852 A1 | 11/2008 | Speelmans et al. | |
| 2009/0004164 A1 | 1/2009 | Speelmans et al. | |
| 2009/0011078 A1 | 1/2009 | Johnson | |
| 2009/0022852 A1 | 1/2009 | Simmons et al. | |
| 2009/0035813 A1 | 2/2009 | Sprenger et al. | |
| 2009/0041736 A1 | 2/2009 | Sprenger et al. | |
| 2010/0016214 A1 | 1/2010 | Sawatzki et al. | |
| 2010/0069322 A1 | 3/2010 | Sinclair et al. | |
| 2010/0215738 A1 | 8/2010 | Ritter et al. | |
| 2011/0065152 A1 | 3/2011 | Avalakki et al. | |
| 2011/0086093 A1 | 4/2011 | Ritter | |
| 2011/0189148 A1 | 8/2011 | Ritter | |
| 2011/0223248 A1 | 9/2011 | Ritter et al. | |
| 2011/0236480 A1 | 9/2011 | Ritter et al. | |
| 2011/0287072 A1 | 11/2011 | Ritter et al. | |
| 2013/0034601 A1 | 2/2013 | Ritter | |
| 2013/0165407 A1 | 6/2013 | Ritter et al. | |
| 2013/0177612 A1 | 7/2013 | Ritter et al. | |
| 2013/0244969 A1 | 9/2013 | Ritter et al. | |
| 2013/0316972 A1 | 11/2013 | Ritter et al. | |

FOREIGN PATENT DOCUMENTS

| | | | |
|---|---|---|---|
| CA | 2056167 A1 | 5/1993 | |
| CA | 2532062 A1 | 7/2006 | |

(56) References Cited

FOREIGN PATENT DOCUMENTS

| | | |
|---|---|---|
| CN | 101366734 | 2/2009 |
| CN | 101396048 A | 4/2009 |
| CN | 101926831 A | 12/2010 |
| DE | 20202562 U1 | 5/2002 |
| DE | 202005009120 U1 | 11/2005 |
| EP | 0272095 A2 | 6/1988 |
| EP | 0474230 A1 | 3/1992 |
| EP | 0458358 B1 | 5/1994 |
| EP | 0199535 B2 | 11/1995 |
| EP | 0549478 B1 | 9/1997 |
| EP | 1175905 A1 | 1/2002 |
| EP | 1195095 A2 | 4/2002 |
| EP | 1105002 B1 | 7/2002 |
| EP | 0957692 B1 | 8/2003 |
| EP | 0946111 B1 | 2/2004 |
| EP | 1195095 A3 | 2/2004 |
| EP | 1242436 B1 | 11/2004 |
| EP | 1514551 A1 | 3/2005 |
| EP | 1352967 B1 | 8/2005 |
| EP | 1614357 A1 | 1/2006 |
| EP | 0778885 B1 | 11/2006 |
| EP | 1255449 B1 | 3/2007 |
| EP | 1644482 B1 | 4/2007 |
| EP | 1776877 A1 | 4/2007 |
| EP | 1803358 A1 | 7/2007 |
| EP | 1832179 A1 | 9/2007 |
| EP | 1887017 A1 | 2/2008 |
| EP | 1897449 A1 | 3/2008 |
| EP | 1811864 B1 | 5/2008 |
| EP | 1927292 A1 | 6/2008 |
| EP | 1890553 B1 | 8/2008 |
| EP | 1685763 B1 | 11/2008 |
| EP | 1988096 A1 | 11/2008 |
| EP | 1513541 B1 | 1/2009 |
| EP | 2014181 A2 | 1/2009 |
| EP | 2027853 A1 | 2/2009 |
| EP | 1965669 B1 | 9/2009 |
| JP | 60-078540 | 5/1985 |
| JP | 61063618 A | 4/1986 |
| KR | 10-2003-0064030 | 7/2003 |
| WO | WO 91/17672 A1 | 11/1991 |
| WO | WO 97/02829 A2 | 1/1997 |
| WO | WO 97/02829 A3 | 3/1997 |
| WO | WO 00/61155 A1 | 10/2000 |
| WO | WO01/64225 * | 9/2001 |
| WO | WO 01/64225 A1 | 9/2001 |
| WO | WO 02/18614 A1 | 3/2002 |
| WO | WO 02/062363 A1 | 8/2002 |
| WO | WO 02/080946 A1 | 12/2002 |
| WO | WO 02/102168 A1 | 12/2002 |
| WO | WO 03/041512 A1 | 5/2003 |
| WO | WO 02/060276 A8 | 10/2003 |
| WO | WO 03/090546 A1 | 11/2003 |
| WO | WO 2004013343 A2 * | 2/2004 |
| WO | WO 2004/013343 A3 | 6/2004 |
| WO | WO 2004/052121 A1 | 6/2004 |
| WO | WO 2004/067013 A1 | 8/2004 |
| WO | WO 2004/093571 A1 | 11/2004 |
| WO | WO 2004/098622 A2 | 11/2004 |
| WO | WO 2004/098622 A3 | 3/2005 |
| WO | WO 2006/113027 A2 | 10/2006 |
| WO | WO 2007/009529 A2 | 1/2007 |
| WO | WO 2007/023226 A2 | 3/2007 |
| WO | WO 2007/054459 A2 | 5/2007 |
| WO | WO 2007/023226 A3 | 6/2007 |
| WO | WO 2007/054459 A3 | 7/2007 |
| WO | WO 2007/095425 A1 | 8/2007 |
| WO | WO 2007/104268 A1 | 9/2007 |
| WO | WO 2007/105945 A2 | 9/2007 |
| WO | WO 2007/105945 A3 | 11/2007 |
| WO | WO 2007/124596 A1 | 11/2007 |
| WO | WO 2007/125558 A1 | 11/2007 |
| WO | WO 2006/113027 A3 | 12/2007 |
| WO | WO 2008/041843 A1 | 4/2008 |
| WO | WO 2008/054193 A1 | 5/2008 |
| WO | WO 2008/091756 A1 | 7/2008 |
| WO | WO 2008/103023 A1 | 8/2008 |
| WO | WO 2008/111832 A1 | 9/2008 |
| WO | WO 2008/127134 A1 | 10/2008 |
| WO | WO 2008/128345 A1 | 10/2008 |
| WO | WO 2008/135959 A1 | 11/2008 |
| WO | WO 2008/153377 A1 | 12/2008 |
| WO | WO 2008/153391 A2 | 12/2008 |
| WO | WO 2008/156354 A1 | 12/2008 |
| WO | WO 2009/008717 A1 | 1/2009 |
| WO | WO 2008/153391 A3 | 2/2009 |
| WO | WO 2009/024429 A2 | 2/2009 |
| WO | WO 2009/113030 A2 | 9/2009 |
| WO | WO 2009/024429 A3 | 12/2009 |
| WO | WO 2009/113030 A3 | 12/2009 |
| WO | WO 2010/008491 A2 | 1/2010 |
| WO | WO 2010/008491 A3 | 3/2010 |
| WO | WO 2010/098822 A1 | 9/2010 |
| WO | WO 2010/105207 A1 | 9/2010 |
| WO | WO 2010/136742 A1 | 12/2010 |
| WO | WO 2011/016008 A1 | 2/2011 |

OTHER PUBLICATIONS

Manzi, et al. New functional milk-based products in the Italian market. Food Chemistry. 2007; 104(2):808-813.
Martini, et al. Lactose digestion from yogurt: influence of a meal and additional lactose. Am J Clin Nutr. 1991; 53(5):1253-1258.
National Digestive Disease. Lactose Intolerance. Available at http://www.niddk.nih.gov/health/digest/pubs/lactose/lactose.htm. Accessed May 17, 1999.
Onwulata, et al. Relative efficiency of yogurt, sweet acidophilus milk, hydrolyzed-lactose milk, and a commercial lactase tablet in alleviating lactose maldigestion. Am J Clin Nutr. 1989; 49(6):1233-1237.
Suarez, et al. A comparison of symptoms after the consumption of milk or lactose-hydrolyzed milk by people with self-reported severe lactose intolerance. N Engl J Med. Jul. 6, 1995;333(1):1-4.
Arunachalam, et al. Role of Bifidobacteria in nutrition, medicine and technology. Nutrition Research. 1999; 19(10):1559-1597.
Bartram, et al. Does yogurt enriched with Bifidobacterium longum affect colonic microbiology and fecal metabolites in health subjects? Am J Clin Nutr. Feb. 1994;59(2):428-32.
Bond, et al. Colonic conservation of malabsorbed carbohydrates. Gastroenterology, 78, 444-447, 1980.
Briet, et al. Improved clinical tolerance to chronic lactose ingestion in subjects with lactose intolerance: a placebo effect? Gut, 41, 632-635, 1997.
Broussalian, et al. Influence of lactose concentration of milk and yogurt on growth rate of rats. J Dairy Science, 66 (3), 438-443, 1983.
Collins, et al. Proximate, Nutritional and Microbiological Analyses of Milk-Sweet Potato Mixtures Fermented with Yogurt Bacteria. Journal of Food Science. 1991; 56:682-684.
Ekstrom, et al. Effects of a diet containing 40% dried whey on the performance and lactase activities in the small intestine and cecum of Hampshire and Chester white pigs. Journal of Animal Science, 42, 106-113, 1976.
Ekstrom, et al. Effect of diets containing dried whey on the lactase activity of the small intestinal mucosa and the contents of the small intestine and cecum of the pig. Journal of Nutrition, 105, 851-860, 1975.
Engstrom, et al. Intestinal disaccharidase activities of three breeds of swine. Journal of Animal Science, 48, 1349-1356, 1979.
Gibson, et al. Enrichment of bifidobacteria from human gut contents by oligofructose using continuous culture. FEMS Microbiol Lett. May 1, 1994;118(1-2):121-127.
Gibson, et al. Selective stimulation of bifidobacteria in the human colon by oligofructose and inulin. Gastroenterology. Apr. 1995;108(4):975-82.
Gomes, et al. Bifidobacterium spp. and Lactobacillus acidophilus: biological, biochemical, technological and therapeutical properties relevant for use as probiotics. Trends in Food Science and Technology. 1999; 10:139-157.
He, et al. Colonic fermentation may play a role in lactose intolerance in humans. Journal of Nutrition, 136, 58-63, 2006.

(56) References Cited

OTHER PUBLICATIONS

Hertzler, et al. Fecal hydrogen production and consumption measurements: response to daily lactose ingestion by lactose maldigesters. Digestive Diseases and Sciences, 42 (2), 348-353, 1997.
Johnson, et al. Adaptation of lactose maldigesters to continued milk intakes. American Journal of Clinical Nutrition. 58, 879-881, 1993.
Kim, et al. In vitro measurements of the lactase activity and the fermentation products of lactose in the cecal and colonic contents of rats fed a control or 30% lactose diet. Journal of Nutrition, 109, 856-63, 1979.
Landon, et al. A double-blind test of the ability of lactagen formula to reduce symptoms of lactose intolerance. Lactagen Clinical Study. Published Jun. 28, 2005 at www.lactagen.com.
Landon, et al. A randomized controlled trial to evaluate effectiveness of a pre- and probiotic formula to treat patients with self-reported severe intolerance to dairy products. Poster presentation at FASEB meeting, Apr. 1-5, 2006. San Francisco, CA. (Poster).
Landon, et al. A randomized trial of a pre- and probiotic formula to reduce symptoms of dairy products in patients with dairy intolerance. Meeting Abstract. FASEB meeting, Apr. 1-5, 2006. San Francisco, CA. p. A1053.
Martini, et al. Strains and species of lactic acid bacteria in fermented milks (yogurts): effect on in vivo lactose digestion. Am J Clin Nutr. Dec. 1991;54(6):1041-6.
Metagenics' Product Catalog—Science-based nutraceuticals for improved patient health. Published Oct. 15, 2006 at www.metagenics.com.
Perman, et al. Role of pH in production of hydrogen from carbohydrates by colonic bacterial flora. Journal of Clinical Investigation. 67, 643-650, 1981.
Pribila, et al. Improved lactose digestion and intolerance among African-American adolescent girls fed a dairy-rich diet. Journal of the American Dietetic Association, 100 (5), 524-528, 2000.
Roberfroid, M. Prebiotics and probiotics: are they functional foods? Am J Clin Nutr. Jun. 2000 ;71(6 Suppl):1682S-7S.
Siddons, et al. The influence of the intestinal mciroflora on disaccharidase activities in the chick. British Journal of Nutrition, 27, 101-112, 1972.
Wang, et al. Effects of the in vitro fermentation of oligofructose and inulin by bacteria growing in the human large intestine. J Appl Bacteriol. Oct. 1993;75(4):373-80.
Wen, et al. Lactose feeding in lactose-intolerant monkeys. American Journal of Clinical Nutrition. 26, 1224-1228, 1973.
Zhong, et al. The role of colonic microbiotica in lactose intolerance. Digestive Diseases and Sciences, 49 (1), 78-83, 2004.
Hamilton, Great Smokies Diagnostic Laboratory Application Guide. Lactose Intolerance Breath Test. Asheville, 1996.
McBean, Dairy Council Digest. National Dairy Council: Rosemont, IL, Mar./Apr. 1994, vol. 65, #2.
Great Smokies Diagnostic Laboratory, Was it something you ate or drank? http://www.gsdl.com/NP/services/patbroch/actpb.html, 1995-6.
National Digestive Diseases Information Clearinghouse. Lactose Intolerance. http://niddk.nih.gov/LactoseIntolerance/LactoseIntolerance.html, Apr. 1994.
Cure Your lactose Intolerance!, advertisement for the Daily Brum Classified, Monday, Jan. 12, 1998, p. 39.
International search report dated Feb. 2, 2010 for PCT Application No. US2009/03834.
International search report dated Mar. 31, 2006 for PCT Application No. US2005/26095.
International search report dated Jun. 14, 2007 for PCT Application No. US2007/061464.
Office action dated Jan. 26, 2010 for U.S. Appl. No. 11/670,198.
Office action dated Mar. 8, 2001 for U.S. Appl. No. 09/346,479.
Office action dated Mar. 19, 2010 for U.S. Appl. No. 12/013,161.
Office action dated Jul. 11, 2007 for U.S. Appl. No. 11/330,369.
Office action dated Sep. 28, 2000 for U.S. Appl. No. 09/346,479.
Office action dated Nov. 29, 2001 for U.S. Appl. No. 09/346,479.
U.S. Appl. No. 12/996,975, filed Feb. 28, 2011, Ritter et al.
U.S. Appl. No. 13/083,340, filed Apr. 8, 2011, Ritter et al.
Keepkidshealth.com. Infant Formula. A pediatrician's guide to your children's health and safety. Available at http://www.keepkidshealthy.com/cgi-bin/MasterPFP.cgi. Accessed on Nov. 10, 2010.
Lactagen. Statement of Use dated Dec. 9, 2005 for U.S. Appl. No. 78/411,486.
Moro, et al. Dosage-related bifidogenic effects of galacto- and fructooligosaccharides in formula-fed term infants. J Pediatr Gastroenterol Nutr. Mar. 2002;34(3):291-5.
Office action dated Aug. 11, 2010 for U.S. Appl. No. 12/013,161.
Office action dated Nov. 22, 2010 for U.S. Appl. No. 11/632,289.
Saavedra, et al. Feeding of Bifidobacterium bifidum and Streptococcus thermophilus to infants in hospital for prevention of diarrhoea and shedding of rotavirus. Lancet. Oct. 15, 1994;344(8929):1046-9.
U.S. Appl. No. 14/062,530, filed Oct. 24, 2013, Ritter.
Office action dated Jul. 24, 2013 for U.S. Appl. No. 13/629,926.
Office action dated Oct. 4, 2013 for U.S. Appl. No. 12/996,975.
Office action dated Feb. 4, 2013 for U.S. Appl. No. 13/629,926.
U.S. Appl. No. 13/629,926, filed Sep. 28, 2012, Ritter.
Office action dated Jun. 28, 2012 for U.S. Appl. No. 12/973,501.
Office action dated Aug. 9, 2011 for U.S. Appl. No. 11/632,289.
Office action dated Oct. 31, 2011 for U.S. Appl. No. 12/973,501.
Rinne, et al. Similar bifidogenic effects of prebiotic-supplemented partially hydrolyzed infant formula and breastfeeding on infant gut microbiota. FEMS Immunol Med Microbiol. Jan. 1, 2005;43(1):59-65.
U.S. Appl. No. 14/171,262, filed Feb. 3, 2014, Ritter.
U.S. Appl. No. 14/293,784, filed Jun. 2, 2014, Ritter et al.
U.S. Appl. No. 14/362,020, filed May 30, 2014, Ritter et al.
Advanced Dairy Chemistry, vol. 3, Apr. 1, 2009, p. 156 "5.5.2~-Galactooligosaccharides."
Albaytak et al. Immobilization of beta-galactosidase on fibrous matrix by polyethyleneimine for production of galacto-oligosaccharides from lactose. Biotechnology progress. 2005; 18(2):p. 240-51.
Alles, et al. Fate of fructo-oligosaccharides in the human intestine. Br J Nutr. 1996.76(2):211-221.
Alliet, et al. An infant formula containing a specific prebiotic mixture ofGOS/IcFOS leads to higher faecal secretory IgA in infants. JPGN Journal of Pediatric Gastroenterology and Nutrition. 2007; 44:120.
Alliet, et al. Effect of prebiotic galacto-oligosaccharide, long-chain fructo oligosaccharide infant formula on serum cholesterol and triacylglycerollevels. Nutrition. 2007; 23:719-723.
Amaretti, et al. Kinetics and metabolism ofBifidobacterium adolescentis MB 239 growing on glucose, galactose, lactose, and galactooligosaccharides. Appl Environ Microbial. Jun. 2007; 73(11):3637-44.
Andersen, et al. Transcriptional and functional analysis of galactooligosaccharide uptake by lacS in Lactobacillus acidophilus. Proc Natl Acad Sci US A. Oct. 25, 2011;108(43): 17785-90. Epub Oct. 17, 2011.
Ansel, H.C., Allen, Jr., L.V., Popovich, N.G. (1999) Pharmaceutical Dosage Forms and Drug Delivery Systems. Published by Lippincott Williams & Wilkins, p. 60-1 00.
Anthony, et al. 90-Day oral (gavage) study in rats with galactooligosaccharides syrup. Food Chem.Toxicol. 2006; 44(6):819-826.
Appel, et al. Effects of dietary galactooligosaccharide on azaserine-induced acinar pancreatic carcinogenesis in male Wistar rats. Nutr Cancer. 1997; 29(1):35-41.
Asakuma, et al. Sialyl oligosaccharides of human colostrum: changes in concentration during the first three days oflactation. Biosci Biotechnol Biochem. Jun. 2007;71(6): 1447-51.
Bakker-Zierikzee, et al. Effects of infant formula containing a mixture of galacto- and fructo-oligosaccharides or viable Bifidobacterium animalis on the intestinal microflora during the first 4 months oflife. Br J Nutr. 2005;94:783-790.
Ballongue. Bifidobacteria and probiotic action in lactic acid bacteria. S Selminen, A von Wright (eds). New York, Marcel Dekker, 1993, 357-428.

(56) References Cited

OTHER PUBLICATIONS

Barger-Lux, et al. The role of calcium intake in preventing bone fragility, hypertension and certain cancers. Journal of Nutrition, 124, 1406S-1411S, 1994.

Barrangou, et al. Functional and comparative genomic analyses of an operon involved in fructooligosaccharide utilization by Lactobacillus acidophilus. Proc Natl Acad Sci US A. Jul. 22, 2003;100(15):8957-62.

Ben XM, LiJ, Feng ZT et al. Low levels of galacto-oligosaccharride in infant formula stimulates growth of intestinal Bifidobacteria and Lactobacilli. 2008;14(2):6564-6568.

Ben, et al. Supplementation of milk formula with galacto-oligosaccharides improves intestinal micro-flora and fermentation in term infants. Chin Med J (Engl). 2004;117:927-931.

Bhatnagar, et al. Lactose intolerance. BMJ, 334, 1331-1332, Jun. 30, 2007.

Boehm, et al. Supplementation of a bovine milk formula with an oligosaccharide mixture increases counts of faecal bifidobacteria in preterm infants. Arch Dis Child Fetal Neonatal Ed. 2002; 86:F178-81.

Bongers, et al. The clinical effect of a new infant formula in term infants with constipation: a double-blind, randomized cross-over trial. Nutrition Journal. 2007;6:8.

Bongers, et al.. The clinical effect of a new infant formula in term infants with constipation: A double-blind, randomized trial. JPGN Journal of Pediatric Gastroenterology and Nutrition. 2005;4I:S78.

Bouhnik, et al. Lactulose ingestion increases faecal bifidobacterial counts: a randomised double-blind study in healthy humans. Eur J Clin Nutr. Mar. 2004; 58(3):462-6.

Bouhnik, et al. The capacity of nondigestible carbohydrates to stimulate fecal bifidobacteria in healthy humans: a double-blind, randomized, placebo-controlled, parallel-group, dose-response relation study. Am J Clin Nutr. Dec. 2004; 80(6):1658-64.

Brannon, et al. NIH Consensus Development Conference Statement: Lactose Intolerance and Health. NIH Cousens State Sci Statements. Feb. 24, 2010; 27(2).

Briet, et al. Bacterial adaptation in patients with short bowel and colon in continuity. Gastroenterology. Nov. 1995; 109(5):1446-53.

Bruins, M.E. Oligosaccharide Production with Thermophilic Enzymes. Thesis. Wageningen Universiteit, 2003. ISBN 9058088405.

Buchowski, et al. Dietary calcium intake in lactose maldigesting intolerant and tolerant African-American women. Journal of the American College of Nutrition, 21 (1), 47-54,2002.

Cashman. Prebiotics and Calcium Bioavailability. In: Chapter 6, Tannock G, ed. Probiotics and Prebiotics: Where Are We Going?. University of Otago, Dunedin: New Zealand. 2002;149-174.

Cheeseman Director, Office of Food Additive Safety, Food and Drug Administration. Letter to Constance Francis Ph.D., GTC Nutrition Golden, CO 80401, Sep. 4, 2009 Re: Agency Response Letter GRAS Notice No. GRN 000286.

Chen et al. Synthesis of galacto-oligosaccharides by immobilized Bacillus stearothermophilus. Acta microbiologica Sinica. 2001;41(3):357-62. (in Chinese with English abstract).

Cheng et al. Production of high-content galacto-oligosaccharide by enzyme catalysis and fermentation with Kluyveromyces marxianus. Biotechnology Letters. 2006;28(11):793-7.

Chockchaisawasdee et al. Synthesis of galacto-oligosaccharide from lactose using beta-galactosidase from Kluyveromyces lactis: Studies on batch and continuous UF membrane-fitted bioreactors. Biotechnology and bioengineering. 2005;89(4):434-43.

Chonan, et al. Undigestibility of galactooligosaccharides. Nihon Shokuhin Kagaku Kogakkaishi. 2004; 51(1):28-33.

Chouraqui et al. Assessment of the safety, tolerance, and protective effect against diarrhea of infant formulas containing mixtures of probiotics or probiotics and prebiotics in a randomized controlled trial. Am J Clin Nutr. 2008; 87 (5): 1365-73.

Crittenden, R. G. Prebiotics. Probiotics: A Critical Review. Tannock, G. (ed) Horizon Scientific Press, Wymondham. 1999; 141-156, 157.

Curda, et al. Dried buttermilk containing galactooligosaccharides—process layout and its verification. Journal of Food Engineering. Dec. 2006; 77(3):468-471.

De Vrese, et al. Probiotics, prebiotics, and synbiotics. Adv Biochem Eng Biotechnol. 2008; 111:1-66.

De Vrese, et al. Probiotics-compensation for lactase insufficiency. American Journal of Clinical Nutrition, 2001;73 (supplement):421S-429S.

De Vries, W., Stouthamer, A.H. (1968) Fermentation of Glucose, Lactose, Galactose, Mannitol, and Xylose by Bifidobacteria. Journal of Bacteriology, vol. 96, No. 2, p. 472-478.

Deguchi, et al. Effects of beta-1-4 galactooligosaccharides administration on defecation of healthy volunteers with constipation tendency. Japanese Journal of Nutrition. 1997;55:13-22.

Delmont. (Ed.). Milk intolerances and rejection. Karger, Basel, 1983.

Depeint et al. Prebiotic evaluation of a novel galactooligosaccharide mixture produced by the enzymatic activity of Bifidobacterium bifidum NCIMB 41171, in healthy humans: a randomized, double-blind, crossover, placebo-controlled intervention study. Am J Clin Nutr. 2008; 87(3):785-91.

Di Stefano, et al. Lactose malabsorption and intolerance and peak bone mass. Gastroenterology. Jun. 2002; 122 (7):1793-9.

Donovan. Human milk oligosaccharides—the plot thickens. Br J Nutr. May 2009;101(9):1267-9. Epub Dec. 15, 2008.

Drakoularakou, et al. A double-blind, placebo-controlled, randomized human study assessing the capacity of a novel galacto-oligosaccharide mixture in reducing travellers' diarrhea. Eur J Clin Nutr. 2010; 64:146-152.

Drossman. The functional gastrointestinal disorders and the Rome III process. Gastroenterology. Apr. 2006; 130 (5):1377-90.

European search report dated and opinion Aug. 30, 2013 for EP Application No. 11775567.8.

Fanaro, et al. Galacto-oligosaccharides are bifidogenic and safe at weaning: A double-blind randomized multicenter study. J Pediatr Gastroenterol Nutr. 2009;48:82-88.

Fisler. Cardiac effects of starvation and semistarvation diets: safety and mechanisms of action. Am J Clin Nutr. Jul. 1992 ; 56(1 Suppl):230S-234S.

Flourie, et al. Can diarrhea induced by lactulose be reduced by prolonged ingestion of lactulose? Am J Clin Nutr. Sep. 1993; 58(3):369-75.

Gershon-Cohen, et al. The relationship of dietary calcium to osteoporosis. Metabolism, Clinical and Experimental. 1964; 13(3):221-226. DOI: 10.1016/0026-0495(64)90101-5.

Gibson, et al. Dietary modulation of the human colonic microbiota: Updating the concept of prebiotics. Nutrition Research Reviews. 2004;17:259-275.

Gibson, et al. Dietary modulation of the human colonic microbiota: introducing the concept of prebiotics. J Nutr. Jun. 1995;125(6):1401-12.

Gibson, et al. Regulatory effects of bifidobacteria on the growth of other colonic bacteria. J Appl Bacterial. 1994; 77:412-420.

Gibson. Dietary modulation of the human gut micro flora using the prebiotics oligofructose and inulin. Journal of Nutrition. 1999; 129(75):14385-14415.

Goulas, et al. Development of a process for the production and purification of alpha- and beta-galactooligosaccharides from Bifobacterium bifidum NCIMB 41171. International Dairy Journal. 2007; 17 (6):648-656.

GTC Nutrition Purimune High Purity GOS webpage. Available at http://www.gtcnutrition.com/EN/products/purimune/index.php. Accessed Feb. 8, 2010.

GTC Nutrition Slides—Introducing Pruimune. Sep. 22, 2009.

Hamilton-Miller. Probiotics and prebiotics in the elderly. Postgrad Med J. 2004;80(946):44 7-51.

He, et al. Effects of yogurt and bifidobacteria supplementation on the colonic microbiota in lactose-intolerant subjects. J Applied Microbial. 2008; 104(2):595-604.

He, et al. The role of colonic metabolism in lactose intolerance. Eur J Clin Invest. 2008;38(8):541-54 7.

He. Dissertation—Lactose intolerance: the role of colonic metabolism. Drukkerij C. Regenboog, Groningen, The Netherlands. 2006.

(56) References Cited

OTHER PUBLICATIONS

Hoover. Bifidobacterium. In The Encyclopedia of Food Microbiology. Carl Batt and P.D. Patel (Eds). Academic Press, San Diego. 2000; 210-217.
Hsu, et al. Enzymatic production of galactooligosaccharides by beta-galactosidase from Bifidobacterium longum BCRC 15708. Journal of agricultural and food chemistry. 2007;55(6):2225-30.
International search report and written opinion dated Feb. 26, 2013 for PCT/US2012/067488.
International search report and written opinion dated Jun. 20, 2011 for PCT Application No. US2011/034346.
International search report and written opinion dated Mar. 29, 2010 for PCT Application No. US10/00447.
Ito, et al. Effects of Administration of Galactooligosaccharides on the Human Faecal Microflora, Stool Weight and Abdominal Sensation. Microbial Ecology in Health Disease. 1990;3:285-92.
Ito, et al. Effects oftransgalactosylated disaccharides on the human intestinal microflora and their metabolism. J Nutr Sci Vitaminol (Tokyo). 1993;39(3):279-88.
Jackson, et al. Lactose maldigestion, calcium intake and osteoporosis in African-, Asian-and Hispanic-Americans. Journal of the American College ofNutrition, 20 (2), 198S-207S, 2001.
Jiang, et al. Improvement of lactose digestion in humans by ingestion of unfermented milk containing Bifidobacterium longum. J Dairy Sci. 1996; 79:750-757.
Jiang, T., Savaiano, D.A. (1997) In Vitro Lactose Fermentation by Human Colonic Bacteria is Modified by Lactobacillus acidophilus Supplementation. Journal of Nutrition, vol. 127, p. 1489-1495.
Khan, et al. Torsades de pointes: a case with multiple variables. Am J Emerg Med. Jan. 1999;17(1):80-5.
Khan, M.A. (2004) Lactagen Hopes Search Test Does a Body Good. Retrieved on Mar. 31, 2014 [online]. Retrieved from Direct Marketing News, from the internet <http://www .dm news.com/lactagen-hopes-search-test-does-a-body-good/printarticle/84 7921>.
Khanna. The UCLA scleroderma clinical trial consortium gastrointestinal tract (UCLA SCTC GIT 2.0) instrument. Oct. 2011.
Kikuchi, et al. 1996. Effect of two levels oftransgalatosylated oligosaccharide intake in rats associated with human faecal micro flora on bacterial glycolytic activity, end-products of fermentation and bacterial steroid transformation. J. Appl. Bacterial. 80:439-446.
Kirii, et al. Calcium, vitamin D and dairy intake in relation to type 2 diabetes risk in a Japanese cohort. Diabetologia. Dec. 2009; 52(12):2542-50.
Klaenhammer. 2010. Research Report: Comparative Growth of Lactobacillus acidophilus and Different Species and Strains ofBifidobacterium and *Escherichia coli* on the Highly Purified Galactooligosaccharide Preparation, RP-G28. North Carolina State University.
Knol, et al. Increase of faecal bifidobacteria due to dietary oligosaccharides induces a reduction of clinically relevant pathogen germs in the faeces of formula-fed preterm infants. Acta Paediatr Suppl. 2005; 94:31-33.
Knol, et al., Colon microflora in infants fed formula with galacto- and fructo-oligosaccharides: More like breast-fed infants. J Pediatr Gastroenterol Nutr. 2005; 40:36-42.
Kobayashi, et al. 2003. Ninety-day repeated oral dose toxicity study of GOS in rats. Yakuruto Kenkyujo Kenkyu Hokokushu (23):25-42. (English abstract and tables).
Kobayashi, et al. Safety of a novel galacto-oligosaccharide: Genotoxicity and repeated oral dose studies. Hum Exp Toxicol. Oct. 2009; 28(10):619-30.
Kukkonen, et al. Long-term safety and impact on infection rates of postnatal probiotic and prebiotic (synbiotic) treatment: randomized, double-blind, placebo-controlled trial. Pediatrics. Jul. 2008; 122(1):8-12.
Kukkonen, et al. Probiotics and prebiotic galacto-oligosaccharides in the prevention of allergic diseases: A randomized, double-blind, placebo-controlled trial. J Allergy Clin Immunol. 2007; 119: 192-198.
Kullen, et al. Use of DNA sequence of variable regions of the 16SrRNA gene for rapid and accurate identification of bacteria in the Lactobacillus acidophilus complex. J. Appl. Microbial. 2000; 89:511-518.
Kunz, et al. Nutritional and biochemical properties of human milk, Part 1: general aspects, proteins, and carbohydrates. Clin Perinatal. 1999; 26(2):307-333.
Kunz, et al. Oligosaccharides in human milk: structural, functional, and metabolic aspects. Annu Rev Nutr 2000; 20:699-722.
Li, et al. Production of non-monosaccharide and high-purity galactooligosaccharides by immobilized enzyme catalysis and fermentation with immobilized yeast cells. Process Biochemistry. 2008; 43(8):896-899.
Lisker. Book review of Lactose digestion—Clinical and Nuritional Implications. Edited by D.M. Paige Paige DM and Bayless TM. The Johns Hopkins University Press, Baltimore, 1981.
Lu, et al. Recent progress on galacto-oligosaccharides synthesis by microbial beta-galactosidase—a review. Acta microbiologica Sinica. 2008; 48(7):980-5. (in Chinese with English abstract).
Lye, et al. The improvement of hypertension by probiotics: effects on cholesterol, diabetes, renin, and phytoestrogens. Int J Mol Sci. Aug. 27, 2009; 10(9):3755-75.
Maischberger, et al. Production oflactose-free galacto-oligosaccharide mixtures: comparison of two cellobiose dehydrogenases for the selective oxidation oflactose to lactobionic acid. Carbohydrate research. 2008 ; 343( 12):2140-7.
Manzanares, et al. The role of prebiotics and synbiotics in critically ill patients. Curr Opin Clin Nutr Metab Care. Nov. 2008;11(6):782-9.
Matlik, et al. Perceived milk intolerance is related to bone mineral content in 10-to 13-year old female adolescents. Pediatrics 2007; 120(3);e669-77.
Matsumoto, et al. 2004. Effects oftransgalactosylated oligosaccharides mixture (N-GOS) on human intestinal microflora. Chonai Saikingaku Zasshi 18(1):25-35. (English abstract and tables).
Matsumoto, et al. 1993. Galactooligosaccharides. Chapter 5 in Oligosaccharides: Production, Properties and Application. Nakakuki, T. (Ed.). Gordon and Breach Science Publishers. Tokyo. Japanese Technology Reviews, vol. 3, pp. 90-106, 222-225 (Refs).
McBain, et al. Modulation of genotoxic enzyme activities by non-digestible oligosaccharide metabolism in in-vitro human gut bacterial ecosystems. J. Med Microbial. 2001; 50:833-842.
McCarron, et al. Estimated healthcare savings associated with adequate dairy food intake. American Journal of Hypertension. 17 (1), 88-97, 2004.
Morita, et al. The QT syndromes: long and short. Lancet. Aug. 30, 2008;372(9640):750-63.
Moro, et al. A mixture of prebiotic oligosaccharides reduces the incidence of atopic dermatitis during the first six months of age. Arch Dis Child. 2006; 91: 814-819.
Moro, et al. Dietary prebiotic oligosaccharides are detectable in the faeces of formula-fed infants. Acta Paediatr Suppl. 2005;94:27-30.
Moro, et al. Effects of a new mixture of prebiotics on faecal flora and stools in term infants. Acta Paediatr Suppl. Sep. 2003;91(441):77-9.
Nakamura, et al. Molecular ecological analysis of fecal bacterial populations from term infants fed formula supplemented with selected blends of prebiotics. Appl Environ Microbial. Feb. 2009; 75(4):1121-8.
Nakkhara T, et al. Lactose hydrolysis and formation of galactooligosaccharides by a novel immobilized beta-galactosidase from the thermophilic fungus Talaromyces thermophilus. Applied biochemistry and biotechnology. 2006; 129-132:215-25.
Napoli, et al. Bifldogenic effects of feeding infant formula containing galacto-oligosaccharides in healthy formula-fed infants. School of Molecular and Microbial Biosciences, University of Sydney, NSW 2006.
NIH (National Institutes of Health)—Consensus Development Conference: Optimal Calcium Intake. Washington DC. US Department of Health and Human Services, Public Health Service. Jun. 6-8, 1994.
Obermayer-Pietsch, et al. Genetic predisposition for adult lactose intolerance and relation to diet, bone density, and bone fractures. J Bone Miner Res. Jan. 2004; 19(1):42-7.
Office action dated Jan. 10, 2013 for U.S. Appl. No. 13/096,711.
Office action dated Jan. 25, 2012 for U.S. Appl. No. 12/055,936.

(56) References Cited

OTHER PUBLICATIONS

Office action dated Feb. 3, 2010 for U.S. Appl. No. 12/055,936.
Office action dated Feb. 4, 2013 for U.S. Appl. No. 16/629,926.
Office action dated Feb. 11, 2011 for U.S. Appl. No. 12/055,936.
Office action dated Feb. 29, 2012 for U.S. Appl. No. 12/707,037.
Office action dated Mar. 9, 2012 for U.S. Appl. No. 13/198,416.
Office action dated Apr. 9, 2014 for U.S. Appl. No. 11/632,289.
Office action dated Apr. 25, 2014 for U.S. Appl. No. 13/744,242.
Office action dated Jun. 3, 2014 for U.S. Appl. No. 13/770,750.
Office action dated Jun. 26, 2014 for U.S. Appl. No. 13/784,788.
Office action dated Jun. 27, 2014 for U.S. Appl. No. 13/784,769.
Office action dated Aug. 5, 2009 for U.S. Appl. No. 12/055,936.
Office action dated Nov. 14, 2013 for U.S. Appl. No. 13/096,711.
Office action dated Dec. 19, 2012 for U.S. Appl. No. 12/707,037.
Office action dated Dec. 30, 2008 for U.S. Appl. No. 12/055,936.
Ohtsuka, et al. Availability of 4'galactosyllactose (0—D-galactopyranosyl-( 1—4)-0—D-galactopyranosyl-( 1—4)-D-glucopyranose) in rat. J. Nutr. Sci. Vitaminol. 1990; 36(3):265-276.
Ohtsuka, et al. Effects of administration of galactooligosaccharides on faecal character in dogs and cats. Bulletin of the Faculty of Agriculture, Tottori University. 1995; 48:145-149. (English abstract only).
Ohtsuka, et al. Utilization and metabolism of [U-(14)C]4' galactosyl-lactose (0-13-D-galactopyranosyl-( 1 +4)-0-P-D—galactopyranosyl-( 1 +4)-D-glucopyranose) in rats. J Nutr. Sci. Vitaminol. 1991; 37(2):173-184.
Palframan, et al. Effect of pH and dose on the growth of gut bacteria on prebiotic carbohydrates in vitro. Anaerobe. Oct. 2002; 8(5):287-92.
Piirainen, et al. In school-aged children a combination of galacto-oligosaccharides and lactobacillus GG increases bifidobacteria more than lactobacillus GG on its own. Ann Nutr Metab. 2008; 52(3):204-8.
Pittas, et al. Vitamin D and calcium intake in relation to type 2 diabetes in women. Diabetes Care. Mar. 2006; 29(3):650-6.
Puccio, et al. Clinical evaluation of a new starter formula for infants containing live Bifidobacterium longum BL999 and prebiotics. Nutrition. Jan. 2007; 23(1): 1-8.
Rania, et al. Effect of maternal prebiotic supplementation on selected fetal immune parameters. Immunobiology. 2005; 210:420.
Remington, The Science and Practice of Pharmacy, 19th Edition, editor Alfonso R. Gennaro, published by Mack Publishing Company (1995) p. 1396, 1046-1413 and 1617-1620.
Rivero-Urgell, et al. Oligosaccharide: application in infant food. Early Hum Dev. 2001;65 Suppl:S43-52.
Roberfroid, et al. Dietary Fructans. Annu. Rev. Nutr. 1998; 18:117-43.
Ross, et al. The 2011 report on dietary reference intakes for calcium and vitamin D from the Institute of Medicine: what clinicians need to know. J Clin Endocrinol Metab. Jan. 2011; 96(1):53-8. Epub Nov. 29, 2010.
Rowland, et al. The effects of transgalactosylated oligosaccharides on gut flora metabolism in rats associated with a human faecal microflora. J. Appl. Bacterial. 1993; 74:667-674.
Sairanen, et al. Yoghurt containing galacto-oligosaccharides, prunes and linseed reduces the severity of mild constipation in elderly subjects. Eur J Clin Nutr. Dec. 2007; 61(12): 1423-8.
Satokari, et al. Polymerase chain reaction and denaturing gradient gel electrophoresis monitoring of fecal Bifidobacterium populations in a prebiotic and probiotic feeding trial. Syst Appl Microbial. 2001 ;24(2):227-231.
Savaiano, et al. Lactose malabsorption from yogurt, pasteurized yogurt, sweet acidophilus milk, and cultured milk in lactase-deficient individuals. Am J Clin Nutr. Dec. 1984; 40(6):1219-23.
Savaiano. Lactose intolerance: a self-fulfilling prophecy leading to osteoporosis? Nutr Rev. Jun. 2003; 61(6 Pt 1):221-3.
Savino, et al. "Minor" feeding problems during the first months of life: Effect of a partially hydrolysed milk formula containing fructo- and galacto-oligosaccharides. Acta Paediatr Suppl. 2003; 91:86-90.

Sazawal, et al. Efficacy of milk fortified with a probiotic Bifidobacterium lactis (DR-10) and prebiotic galacto-oligosaccharides in prevention of morbidity and on nutritional status. Asia Pac J Clin Nutr. 2004; 13(Suppl):S28.
Schaafsma, et al. Lactose and lactose derivatives as bioactive ingredients in human nutrition. International Dairy Journal. 2008; 18:458-465.
Schmelzle, et al. Randomized double-blind study of the nutritional efficacy and bifidogenicity of a new infant formula containing partially hydrolyzed protein, a high beta-palmitic acid level, and nondigestible oligosaccharides. J Pediatr Gastroenterol Nutr. 2003; 36(3):343-51.
Scholtens, et al. Fecal secretory immunoglobulin A is increased in healthy infants who receive a formula with short-chain galacto-oligosaccharides and long-chain fructo-oligosaccharides. J Nutr. 2008; 138: 1141-1147.
Scholtens, et al.. Bifidogenic effects of solid weaning foods with added prebiotic oligosaccharides: A randomised controlled clinical trial. JPGN Journal of Pediatric Gastroenterology and Nutrition. 2006; 42:553-559.
Schrezenmeir, et al. Probiotics, prebiotics, and synbiotics—approaching a definition. Am J Clin Nutr. Feb. 2001; 73(2 Suppl):361S-364S.
Scrimshaw, N.S., Murray, E.B. (1988) Adaptation of lactose-maldigesting individuals to milk and milk products. American Journal of Clinical Nutrition, vol. 48 (suppl), p. 1118-1119.
Scrimshaw, et al. The acceptability of milk and milk products in populations with a high prevalence of lactose intolerance. Am J Clin Nutr. Oct. 1988;48(4 Suppl): 1079-159.
Sela, et al. The genome sequence of Bifidobacterium longum subsp. infantis reveals adaptations for milk utilization within the infant microbiome. Proc. Natl. Acad. Sci. 105(48) 18964-18969, Dec. 2008.
Shadid, et al. Effects of galactooligosaccharide and long-chain fructooligosaccharide supplementation during pregnancy on maternal and neonatal microbiota and immunity—a randomized, double-blind, placebo-controlled study. Am J Clin Nutr. Nov. 2007; 86(5):1426-37.
Silk, et al. Clinical trial: the effects of a trans-galactooligosaccharide prebiotic on faecal microbiota and symptoms in irritable bowel syndrome. Aliment Pharmacal Ther [advance electronic publication—Dec. 2, 2008].
Smiricky-Tjardes, et al. Dietary galactooligosaccharides affect ileal and total-tract nutrient digestibility, ileal and fecal bacterial concentrations, and ileal fermentative characteristics of growing pigs. J. Anim. Sci. 2003; 81:2535-2545.
Splechtna et al. Process development for the production of prebiotic galactooligosaccharides from lactose using beta-galactosidase from Lactobacillus sp. Biotechnology journal. 2007;2(4):480-5.
Splechtna et al. Production of prebiotic galacto-oligosaccharides from lactose using betagalactosidases from Lactobacillus reuteri. J Agric Food Chern. Jul. 12, 2006; 54(14):4999-5006.
Splechtna, et al. Comparison between discontinuous and continuous lactose conversion processes for the production of prebiotic galacto-oligosaccharides using beta-galactosidase from Lactobacillus reuteri. Journal of agricultural and food chemistry. 2007; 55(16):6772-7.
Splechtna, et al. Production of a lactose-free galacto-oligosaccharide mixture by using selective enzymatic oxidation of lactose into lactobionic acid. Enzyme and Microbial Technology [Enzyme Microb. Technol.]. 2001; 29(6-7):434-440.
Suarez, et al. Tolerance to the daily ingestion of two cups of milk by individuals claiming lactose intolerance. Am J Clin Nutr. May 1997; 65(5): 1502-6.
Szilagyi, et al. Differential impact of lactose/lactase phenotype on colonic microflora. Can J Gastroenterol. Jun. 2010; 24(6):373-9.
Szilagyi, et al. Improved parameters of lactose maldigestion using lactulose. Dig Dis Sci. Jul. 2001; 46(7): 1509-19.
Tanaka, et al. Effects of administration of TOS and Bifidobacterium breve 4006 on the human fecal flora. Bifidobact Microflora. 1983; 2(1):17-24.

(56) References Cited

OTHER PUBLICATIONS

Tarantino. Director, Office of Food Additive Safety, Food and Drug Administration. Letter to Gavin Thompson, Ph.D., Environ International Corp. Arlington, VA. Jul. 28, 2008 Re: Agency Response Letter GRAS Notice No. GRN 000236.

Teuri, et al. Galacto-oligosaccharides relieve constipation in elderly people. Ann Nutr Metab. 1998; 42:319-327.

Teuri, et al. Increased fecal frequency and gastrointestinal symptoms following ingestion of galacto-oligosaccharide-containing yogurt. J Nutr Sci Vitaminol (Tokyo). Jun. 1998; 44(3):46571.

Thomas, et al. Carbohydrate metabolism is essential for the colonization of Streptococcus thermophilus in the digestive tract of gnotobiotic rats. PLoS One. 2011;6(12):e28789. Epub Dec. 22, 2011.

Tuohy, et al. Modulation of the Human Gut Microflora Towards Improved Health Using Prebiotics—Assessment of Efficacy. Current Pharmaceutical Design. 2005; 11:75-90.

Tzortzis, G. Functional properties of the second generation prebiotic galacto-oligosaccharide (B-GOS). Agro Food Industry Hi-Tech, Tekno Scienze, IT. 2009; 20(3), Suppl:43-46.

Van Den Heuvel, et al. Transgalactooligosaccharides Stimulate Calcium Absorption in Postmenopausal Woman. Journal of Nutrition. 2000; 130(12):2938-2942.

Van Den Heuvel, et al.. Nondigestible oligosaccharides do not interfere with calcium and nonheme-iron absorption in young, healthy men. Am J Clin Nutr. 1998; 67:445-451.

Van Dokkum, et al. Effect of nondigestible oligosaccharides on large-bowel functions, blood lipid concentrations and glucose absorption in young healthy male subjects. EurJClinNutr. 1999; 53:1-7.

Van Hoffen, et al. A specific mixture of short-chain galacto-oligosaccharides and long-chain fructo-oligosaccharides induces a beneficial immunoglobulin profile in infants at high risk for allergy. Allergy. 2009; 64:484-487.

Van Meer, et al. Prebiotic oligosaccharides and the enterohepatic circulation of bile salts in rats. Am J Physiol Gastrointest Liver Physiol. Feb. 2009; 294(2):0540-7.

Vulevic, et al. Modulation of the fecal microflora profile and immune function by a novel trans-galactooligosaccharide mixture (B-GOS) in healthy elderly volunteers. Am J Clin Nutr. 2008; 88(5):1438-46.

Wan, et al. The investigation of dietary calcium intake and bone mass development of preschool children in west of China. Bone. 2008; 43:S91. DOI: 10.1016/J.BONE.2008.07.123.

Ward, et al. In vitro fermentation fbreast milk oligosaccharides by Bifidobacterium infantis and Lactobacillus gasseri. Appl Environ Microbial. Jun. 2006;72(6):4497-9.

Wijnands, et al. 1999. A comparison of the effects of dietary cellulose and fermentable galacto-oligosaccharide, in a rat model of colorectal carcinogenesis: Fermentable fiber confers greater protection than non-fermentable fiber in both high and low fat backgrounds. Carcinogenesis 20(4):651-656.

Wijnands, et al. 2001. Effect of dietary galacto-oligosaccharides on azoxymethane-induced aberrant crypt foci and colorectal cancer in Fischer 344 rats. Carcinogenesis 22(1):127-132.

Wisker, et al 1985. Dietary fibre in cereals. In: Pomeranz, Y. (Ed.). Advances in Cereal Science and Technology. American Association of Cereal Chemists; St. Paul, Minn., vol. VII, pp. 169-238.

World Health Organization (WHO). 1993. Annex II. Environmental Health Criteria 104. Principles for the Toxicological Assessment of Pesticide Residues in Food. p. 113.

Yamashita, et al. Production of a-Linked Galactooligosaccharide (a-GOS) by a-Galactosidase from Aspergillus niger APC-9319 and Its Physical and Physiological Properties. J. Appl. Glycosci. 2004; 51:115-121.

Yasutake, et al. 2003. Safety of GOS: bacterial reverse mutation, micronucleus, and chromosomal aberration tests. Yakuruto Kenkyujo Kenkyu Hokokushu 23:13-24. (English abstract and tables).

Zheng et al. Production of galacto-oligosaccharides by immobilized recombinant beta-galactosidase from Aspergillus candidus. Biotechnology journal. 2006;1(12):1464-70.

Ziegler, et al. Term infants fed formula supplemented with selected blends of prebiotics grow normally and have soft stools similar to those reported for breast-fed infants. J Pediatr Gastroenterol Nutr. 2007; 44:359-364.

* cited by examiner

METHODS AND COMPOSITIONS FOR TREATING LACTOSE INTOLERANCE

CROSS-REFERENCE TO RELATED APPLICATION

This application is a continuation of U.S. patent application Ser. No. 11/632,289, filed Dec. 12, 2007 now abandoned which is a 371 of PCT/US05/26095, filed Jul. 22, 2005 which is a continuation-in-part of U.S. utility patent application Ser. No. 10/710,588, filed Jul. 22, 2004, now abandoned all of which are incorporated herein by reference in their entirety.

BACKGROUND OF THE INVENTION

According to several sources, there are 30 to 50 million people in the world who are lactose intolerant. In the 1960's and 1970's, it was reported that 70% of the adults in the world had lactose intolerance. In 1995, it was reported that 75% of the adults in the world and 25% of the adults in the U.S. were categorized as being lactose intolerant. In 1994, it was reported that 75% of African Americans and Native Americans and 90% of Asian Americans had lactose intolerance. It has also been reported that 30% of adults who are mostly North Western and North American descendants of the Europeans, have adapted to high lactase activity into adulthood. Research concludes that this adaption is genetically controlled, permanent and related to a long tradition of milk and milk products consumption in these regions of the world.

If an individual suspects that he has lactose intolerance, it is potentially harmful for him to restrict his diet since it may result in a nutrition shortage or a failure to detect a more serious disease. Mile and other diary products are major sources for nutrition in the basic American diet. The primary nutrients in milk are protein, calcium, riboflavin, vitamin A, and vitamin D. Calcium is an important part of the recommended daily allowances of vitamins and minerals and any deficiency therein can lead to osteoporosis.

Lactose is not digested when the amount of lactose consumed exceeds the lactase enzyme capacity of the small intestine. Instead, excess undigested lactose passes through the small intestines into the large intestine where it is fermented by a bacteria called colinic flora. The fermentation of the lactose in the large intestine produces hydrogen and methane which can lead to bloating, gas, and diarrhea. These symptoms are caused by a very low activity of lactase in the intestines.

Young children who have lactose intolerance are very rare. The amount of lactase enzyme a body produces generally reaches a maximum immediately after birth and then decreases in the majority of people after their body adjusts during the ages of 3-15. A stool test is used to test lactose intolerance in young children. For young children, the breath test is not as accurate because they usually have a tendency to get dehydrated which can cause diarrhea.

The reasons for an onset of lactose intolerance are generally unknown. However, there is a general belief that by consuming small amounts of lactose frequently over a period of time, lactose intolerance can be improved. Whole milk and chocolate milk appear to be tolerated better than low fat milk because the fat content of whole milk and chocolate milk slows the rate of gastric emptying. Previous attempts at improving the symptoms of lactose intolerance have met with some success. See, e.g., Published U.S. Patent Application No. 0020034496 The present invention builds upon this previous success.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The invention provides methods, compositions, kits, and business methods for the reduction of symptoms of lactose intolerance. Symptoms of lactose intolerance include gas, bloating, diarrhea, abdominal pain, cramping, and vomiting. The methods and compositions of the invention reduce or eliminate one or more of these symptoms, typically all of the symptoms. A striking aspect of the present invention is that the reduction or elimination of symptoms persists after treatment has concluded. Thus, the present invention need not be used on a continuous basis but rather may be utilized in a discrete time period and then discontinued.

Lactose Intolerance

Lactose Intolerance, otherwise referred to as lactose maldigestion, is the inability to digest a significant amount of lactose, derived from a deficiency of the lactase enzyme in the small intestine. Lactose is the natural sugar in milk and milk products of all mammals. Lactase is the enzyme which splits the milk sugar lactose into its components (i.e., glucose and galactose), and also breaks down the milk sugar into smaller forms that can be processed into the bloodstream. The lactase enzyme is necessary for mammals to digest lactose.

There is an important distinction between lactose intolerance and milk allergies. Lactose intolerance is the inability of the body to digest lactose-containing products due to a deficiency in the lactase enzyme. A milk allergy, however, is a sensitively to the protein in milk, which involves the immune system and does not relate to a deficiency of the lactase enzyme. In humans, a milk allergy is usually experienced only by infants.

Generally, humans develop lactose intolerance from a primary or secondary cause. The primary cause is an onset of loss of lactase that is a permanent condition. This occurs at a variable period after the weaning period. The primary cause is also genetically determined. The secondary cause is generally a temporary condition that occurs as a result of another disease or event that damages the lining of the small intestine where lactase is active. This is usually caused by an acute diarrheal disease, parasitic infection, Cohn's disease, celiac disease, gastrointestinal surgery, or the intake of certain medications.

In addition to the primary and secondary causes, certain human ethnic and racial populations have more of a predisposition for lactose intolerance. In these populations, social and cultural habits and attitudes influence lactose intolerance. Lactose activity can also decrease with age in certain ethnic and racial populations, including those populations which have origins in Europe, the African plains, and the Siberian Steppes. Humans who are most likely to have or develop lactose intolerance include those of Asian, Middle Eastern, North American, African, and Latin American decent.

Lactose intolerance can be tested either indirectly or directly. There are three main ways to test by the indirect method: a hydrogen breath test, a stool acidity test, or a blood glucose test. In the hydrogen breath test, the breath is measured to determine the amount of hydrogen produced after consuming a measured amount of lactose, typically 15 g. The lactose is consumed by drinking a lactose mixture, and the subject exhales into a vacuum-sealed collection tube at three one hour time intervals. A high level of hydrogen in the breath indicates an improper digestion of lactose. In a stool test, the stool is tested to determine the amount of acid. In a blood glucose test, the blood is tested to determine the amount of glucose (sugar) content after administering a predetermined amount of lactose-containing product to the subject. The direct method measures lactose activity in a mucosal biopsy specimen.

People typically have different systems of lactose intolerance. Lactose intolerance may also be psychologically induced. There are also many different variations of lactose intolerance depending on the individual. For example, some individuals cannot have cheese, melted cheese, plain milk, or warm diary containing products like milk in coffee, while others cannot have any diary products at all. Also, most lactose intolerant people are limited as to the amount of special "lactose free" foods they can eat that have been manufactured by specified companies. Some examples of these "lactose free" foods are: Mocha Mix ice cream, Tofutti ice cream and ice cream sandwiches, LACTAID® brand milk, cheese, Tofutti "Better than Cream Cheese", margarine, and live cultured yogurt. These products are not readily available everywhere.

The use of lactase tablets help lactose intolerant people digest milk and milk products. Each lactase tablet typically hydrolyzes up to 99% of the ingested lactose within 24 hours, and is designed to be ingested with the lactose containing food.

Still other techniques for dealing with lactose maldigestion is to use microgranules containing bioactive compounds or microorganisms. See, e.g., U.S. Pat. No. 5,952,021. The use of an active lactase composition for treatment of lactase deficiency is described in U.S. Pat. No. 3,718,739.

Methods

Methods of the invention include methods of administering lactose in increasing doses to an individual suffering from lactose intolerance. The end result is a reduction or elimination of the symptoms of lactose intolerance in the individual. Methods include the administration of lactose, in increasing doses, for a period of time, to an individual with lactose intolerance. The lactose may be in any form, including liquid or powdered. In some embodiments, other substances are administered in combination with the lactose. "In combination," as used herein, encompasses simultaneous administration of a substance with lactose, as well as administration before lactose (e.g., before a regimen of increasing doses of lactose begins, or before a dose of lactose during such a regimen), after lactose (e.g., after a regimen of increasing doses of lactose begins, or after a dose of lactose during such a regimen), or any combination thereof. Other substances of use in the methods and compositions of the invention besides lactose include live bacteria, fructooligosaccharides, and buffers, e.g., phosphates.

Methods of the invention also include the administration of lactose in increasing doses, in combination with other treatments for lactose intolerance. Other treatments include any of those described herein, such as the use of lactase, or the use of products containing pre-digested lactose.

The invention further provides methods of decreasing the symptoms of lactose intolerance for an extended period of time after treatment stops. Thus, the methods of the invention include partially, substantially, or completely decreasing the symptoms of lactose intolerance for a period of days, weeks, months, years, or permanently. Such a decrease is accomplished by the methods and compositions described herein.

Individuals who may benefit from the methods and compositions of the invention include individuals suffering from the symptoms of lactose intolerance, as described above. Any degree of lactose intolerance may be treated by the methods of the invention. Symptoms of lactose intolerance include gas, bloating, abdominal discomfort, diarrhea, vomiting, and/or cramping. Effectiveness of treatment may be measured in a number of ways. Conventional measurements, such as hydrogen gas production, stool acidity, or blood glucose, may be used before and after treatment. Alternatively, or in addition, the amount of lactose-containing product that may be consumed before the onset of one or more symptoms may be measured or evaluated before and after treatment. Thus, for example, treatment is considered partially effective if, after treatment, on average less hydrogen is produced with a given dose of lactose.

More commonly, individuals will not precisely test the amount of hydrogen or, e.g., use a blood glucose test to measure effectiveness. Instead, individuals generally have a sense of how much lactose-containing product they may consume, and the types and degree of symptoms experienced after such consumption. "Partial" elimination of symptoms of lactose intolerance is any noticeable or measurable increase in the amount of lactose that may be consumed before the onset of symptoms. "Substantial" elimination of symptoms of lactose intolerance, as used herein, encompasses an effect where at least about twice the amount of lactose may be consumed after treatment before the onset of symptoms as could have been consumed before treatment "Complete" or "substantially complete" elimination of symptoms of lactose intolerance, as used herein, indicates that normal amounts of lactose may be consumed after treatment (i.e., the amount of lactose in a typical diet for the area and/or culture in which the individual normally lives) without symptoms, or with only the rare occurrence of symptoms. Thus, for example, an individual may know that if he or she consumes one half cup (4 oz.) of milk that there will be no, or minimal, symptoms, but if 1 or more cup of milk is consumed, then symptoms such as gas or diarrhea occur. The individual may find that, after treatment, 1 and one-half cups of milk may be consumed but that 3 or more cups cause symptoms. This indicates that symptoms of lactose intolerance were substantially eliminated. Alternatively, the individual may find that after treatment a normal diet for their geographical or cultural region may be consumed with no, or rare, symptoms of lactose intolerance. In that case, symptoms of lactose intolerance were completely eliminated.

Alternatively, effectiveness may be measured by percent decrease in symptoms of lactose intolerance. In this measurement, the severity of a predetermined symptom, or set of symptoms is measured before and after treatment, e.g., using pre and post Likert scale. Exemplary symptoms include gas, bloating, diarrhea, cramping, abdominal pain, and vomiting. Any one, or more than one, of the symptoms may be measured. For example, an individual may be asked to rate one or more symptoms on a scale of increasing severity from 1 to 5. In one embodiment, a set of symptoms is rated, and the ratings are added; for example, gas, bloating, diarrhea, abdominal pain, and cramping may be rated. Percentage decrease in symptoms from before to after treatment may be calculated, and the symptoms of lactose intolerance may be considered eliminated by that percent decrease (e.g., if there is a 50% decrease in symptoms, then symptoms of lactose intolerance is 50% eliminated). See, e.g., Example 2.

In some embodiments, the invention provides a method of decreasing symptoms of lactose intolerance in an individual exhibiting symptoms of lactose intolerance by administering to the individual increasing amounts of lactose for a period of time, wherein one or more symptoms of lactose intolerance are partially, substantially, or completely eliminated. In some embodiments, the symptom(s) of lactose intolerance remains partially, substantially, or completely eliminated for at least about 1 day, 1 week, 1 month, 2 months, 3 months, 4 months, 5 months, 6 months, 9 months, one year, 18 months, two years, three years, four years, five years, or more than five years after the termination of treatment, or permanently after the termination of treatment. In some embodiments, the invention provides a method of decreasing symptoms of lactose intolerance in an individual exhibiting symptoms of lactose intolerance by administering to the individual increasing amounts of lactose for a period of time, wherein symptoms of lactose intolerance are substantially eliminated for at least about one month after treatment is terminated.

In some embodiments, the invention provides a method of decreasing symptoms of lactose intolerance in an individual exhibiting symptoms of lactose intolerance by administering to the individual increasing amounts of lactose for a period of time, wherein the symptoms of lactose intolerance, measured as described herein, are decreased by an average of about 10%, 20%, 30%, 40%, 50%, 60%, 70%, 80%, 90%, 95%, or about 100%. An "average" decrease is a decrease as measured in a group of individuals exhibiting symptoms of lactose intolerance, such as more than about 2, 3, 4, 5, 10, 20, or 30 individuals. In some embodiments, the decrease of symptoms of lactose intolerance persists or becomes even greater (e.g., 50% decrease to 55% decrease) for at least about 1 day, 1 week, 1 month, 2 months, 3 months, 4 months, 5 months, 6 months, 9 months, one year, 18 months, two years, three years, four years, five years, or more than five years after the termination of treatment. In some embodiments, the decrease in symptoms is permanent. In some embodiments, the invention provides a method of decreasing symptoms of lactose intolerance in an individual exhibiting symptoms of lactose intolerance by administering to the individual increasing amounts of lactose for a period of time, wherein the symptoms of lactose intolerance, measured as described herein, are decreased by an average of about least about 20% and remain decreased by at least about 20% for at least about one month after treatment is terminated. In some embodiments, the invention provides a method of decreasing symptoms of lactose intolerance in an individual exhibiting symptoms of lactose intolerance by administering to the individual increasing amounts of lactose for a period of time, wherein the symptoms of lactose intolerance, measured as described herein, are decreased by an average of about least about 50% and remain decreased by at least about 50% for at least about one month after treatment is terminated.

The total duration of treatment may be from about two weeks to about 12 weeks, or about four weeks to about ten weeks, or about four weeks to about eight weeks, or about six weeks. During this period of time, the subject is started on a program of taking increasing amounts of the lactose containing product of the invention, optionally along with ingestion of lactose containing food products, and in some embodiments also in combination with other substances, as described herein. In some embodiments, the total duration of treatment is about 15 days to about 90 days, or about 15 days to about 60 days, or about 20 days to about 50 days, or about 20 days to about 40 days, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 days. In some embodiments, the total duration of treatment is about 38 days. In some embodiments, the total duration of treatment is about 42 days. It will be appreciated that these durations are averages, and that individuals using the treatment may vary from the average based on the severity of their symptoms, missing days of treatment, and the like. In some embodiments, the duration of the treatment is based on the individual's symptoms. Thus, an individual may experience a return of symptoms at a given dose of lactose, and may require that they stay at that dose, or a lower dose, until symptoms subside. Thus, in some embodiments, the duration of the treatment is not definitively established at the outset, but continues until the highest dose of lactose is achieved, or until the desired level of lactose tolerance is achieved.

Increasing dosage of lactose may be achieved by increasing the number of doses per day of lactose administered, increasing the amount of lactose per dose, or both. Typically, both strategies are used. Thus, in some embodiments of the invention, lactose is initially administered once per day, at increasing doses, followed by twice per day administration, also at increasing doses. The once per day administration can last for a period of about 6 to 30, or about 10 to 26, or about 14 to 22, or about 16 to 20, or about 18 days, and the twice per day administration can last for a period of about 4 to 28, or about 8 to 24, or about 12 to 20, or about 14 to 28, or about 16 days. In some embodiments, during the twice per day administration, the first dose of lactose is constant while the second dose increases. In some embodiments, lactose may be administered an average of about once per day, twice per day, three, four, five, six, or more than six timer per day, or any combination thereof.

After treatment has concluded, the individual is encouraged to enjoy dairy products at least once every 4-5 days in order to maintain the reduction in symptoms of lactose intolerance.

In some embodiments, the individual self-administers the lactose-containing product. In some embodiments, the lactose-containing product is supplied or recommended by a health professional, e.g., a dietician, nutritionist, nurse, physician, or other qualified health professional. In some embodiments, the lactose-containing product is administered by a health professional and/or results of the program are monitored by a health professional. In some embodiments, the lactose-containing product is labeled as a medical food.

While an individual typically will not require more than one course of treatment, in some embodiments of the invention an individual may have repeated courses of treatment. The course of treatment may be repeated when symptoms of lactose intolerance appear or increase to an undesirable level. Alternatively, the course of treatment may be repeated at regular or predetermined intervals. Thus, treatment may be repeated after about one month, two months, three months, four months, six months, eight months, ten months, one year, 18 months, two years, three years, four years, five years, or more than five years, or any combination thereof (e.g., treatment may be repeated after one year, then every two to five years thereafter). The treatment may be repeated in the same form (e.g., duration, dosage, timing of dosage, additional substances, etc.) as used in the first treatment, or it may be modified. For example, treatment duration may be shortened or lengthened, dosage may be increased more quickly or slowly and/or a higher or lower starting dose of lactose may be used, a different lactose-containing product may be used (e.g., containing more or less of other substances, or fewer or more substances in addition to lactose), and the like.

The starting dose of lactose and the incremental increases in lactose dosage may be any suitable dose size. In some embodiments, the starting dose of lactose is about 0.05 to 4.0 gm, or about 0.1 to about 3 gm, or about 0.2 to about 3.0 gm, or about 0.2 to about 2 gm, or about 0.4 to about 1.6 gm, or about 0.4 to about 1.4 gm, or about 0.6 to about 1.2 gm, or about 0.6 to about 1.0 gm, or about 0.7 to about 0.9 gm, or about 0.8 gm. The incremental increase in lactose dosage can vary, or each increase can be the same, or any combination thereof. The lactose dosage may increase incrementally by about 0.05 to 4.0 gm, or about 0.1 to about 3 gm, or about 0.2 to about 3.0 gm, or about 0.2 to about 2 gm, or about 0.4 to about 1.6 gm, or about 0.4 to about 1.4 gm, or about 0.6 to about 1.2 gm, or about 0.6 to about 1.0 gm, or about 0.7 to about 0.9 gm, or about 0.8 gm. The maximum dose reached in treatment again may be any suitable dose size, depending on the individual being treated and the outcome desired. The maximum dose of lactose may be about 6 to about 60 gm, or about 12 to about 48 gm, or about 14 to about 36 gm, or about 16 to about 36 gm, or about 18 to about 34 gm, or about 20 to about 32 gm, or about 22 to about 30 gm, or about 23 to about 29 gm, or about 24 to about 28 gm, or about 25 to about 27 gm, or about 25.5 to about 26.5 gm, or about 25.5, 25.6, 25.7 gm.

Thus, in some embodiments of the invention, the initial dose of lactose is about 0.8 gm, and the dose is increased by 0.8 gm over time, for example, daily, until a maximum dose of 25.6 gm of lactose is reached. Additional phases of the regimen may include giving various amounts of milk products in which the dosage of lactose may be given in dairy form, before the treatment ends, and the dosage of lactose in the milk products may not be precisely the same as the doses given up to that point; it will be understood that various milk products and brands of milk products may contain varying doses of lactose.

The lactose may be given in any suitable form, i.e., as a powder, such as in capsules or tablets, or powder that may be dissolved in a liquid prior to consumption, or in liquid form, e.g., predissolved in a liquid or in the form of milk. Any grade or form of lactose that is suitable for consumption by the individual being treated, e.g., by humans, may be used. Lactose-containing products useful in the invention are described more fully below.

Additional substances may be given in conjunction with lactose. These substances can enhance the action of the increasing doses of lactose by, e.g., encouraging the growth of bacteria in the gut that alleviate symptoms of lactose intolerance, increasing adhesion of friendly bacteria, or allowing doses of friendly bacteria to more readily pass through the stomach without being destroyed. These substances may be given prior to treatment with lactose, during treatment with lactose, after treatment with lactose, or any combination thereof. If administered during lactose treatment, they may be administered with the dose of lactose being given, or before or after the dose of lactose, or any combination thereof.

Substances of use in the invention in conjunction with lactose include live bacteria, fructooligosaccharides (FOS), and buffers, e.g., phosphates. One or more of these substances may be used in combination with lactose at any suitable time before, during, after treatment, or some combination thereof. Thus, in some embodiments, during some or all of the treatment, lactose is administered in conjunction with live bacteria. In some embodiments, during some or all of the treatment, lactose is administered in conjunction with FOS. In some embodiments, during some or all of the treatment, lactose is administered in conjunction with buffer, e.g., phosphates. In some embodiments, during some or all of the treatment, lactose is administered in conjunction with live bacteria and FOS. In some embodiments, during some or all of the treatment, lactose is administered in conjunction with live bacteria and phosphates. In some embodiments, during some or all of the treatment, lactose is administered in conjunction with FOS and buffer, e.g., phosphates. In some embodiments, during some or all of the treatment, lactose is administered in conjunction with live bacteria, FOS and buffer, e.g., phosphates Live bacteria, e.g., live cultured bacteria, that may be used in the methods and compositions of the invention include any suitable bacteria for assisting in reduction or elimination of the symptoms of lactose intolerance. Typically such bacteria will be probiotic. Probiotic bacteria favorably alter the intestinal microflora balance, inhibit the growth of harmful bacteria, promote good digestion, boost immune function, and increase resistance to infection. People with flourishing intestinal colonies of beneficial bacteria are better equipped to fight the growth of disease-causing bacteria. Probiotic bacteria such as *lactobacilli* and *bifidobacteria* are thought to maintain a healthy balance of intestinal flora by producing organic compounds, such as lactic acid, hydrogen peroxide, and acetic acid, that increase the acidity of the intestine and inhibit the reproduction of many harmful bacteria. Probiotic bacteria also produce substances called bacteriocins, which act as natural antibiotics to kill undesirable microorganisms. Nonexclusive examples of probiotic bacteria that may be used in the methods of the invention include *L. acidophilus* or *lactobacillus acidophilus*. *Acidophilus*, a probiotic, is one of the most important strains of the *Lactobacilli* family of microflora which inhabit the gastrointestinal tract. These "good" bacteria are involved with immune system function, inhibiting carcinogenesis, metabolism of cholesterol, aging, and nutritional status. *Acidophilus* and other probiotic bacteria help maintain optimum pH, reduce putrefaction, and reduce endotoxemia. Other *lactobacillus* bacteria which may be employed include *lactobacillus crispatus, lactobacillus casei, lactobacillus rhamnosus, lactobacillus reuteri, lactobacillus fermentum, L. plantarum, L. sporogenes, L. bulgaricus* and *lactobacillus rhamnosus*. Other probiotic bacteria include *Bifidobacterium lactis, B. bifidum, B. infantis, Saccharomyces boulardii*. The bacteria may be given as part of a food, e.g., in yogurt, or in powdered form. Mixtures of one or more species or strains of bacteria may be used.

In some embodiments, probiotic bacteria, such as *L. acidophilus*, is given prior to beginning treatment with lactose. In some embodiments, probiotic bacteria, such as *L. acidophilus*, is given in conjunction with treatment with lactose, for part or all of the treatment with lactose. Thus, in some embodiments, some or all doses of lactose are accompanied by a dose of bacteria, e.g. live cultured bacteria, e.g., *L. acidophilus*. In some embodiments, bacteria, e.g., *L. acidophilus* is given initially with the lactose, but then its use is discontinued. For example, the initial one, two, three, four, five, six, seven, eight, nine, ten, or more than ten days of treatment with lactose may include doses of bacteria, with the use of bacteria discontinued after that time. In some embodiments, bacteria, e.g. bacteria in yogurt, or bacteria by themselves, may be given for the first two days of treatment, then the administration of bacteria is discontinued. In some embodiments, probiotic bacteria, either alone or in combination with other substances or treatments are used after the treatment with lactose is terminated. The bacteria may be taken for any suitable period after the termination of treatment with lactose, and may be taken daily or at regular or irregular intervals. Doses may be as described below.

Any suitable dosage of bacteria may be used. Typically, bacteria are given as live cultured bacteria, e.g., in combination with lactose and, optionally, other substances. The dose can be about 1 to about 1000 mg, or about 2 to about 200 mg, or about 2 to about 100 mg, or about 2 to about 50 mg, or about 4 to about 25 mg, or about 5 to about 20 mg, or about 10 to about 15 mg, or about 10, 11, 12, 12.5, 13, 14, or 15 mg. In some embodiments, *L. acidophilus* is used in a dose of about 12.5 mg. The dose may be given in combination with lactose. In some embodiments, as lactose dose increases, the dose of bacteria increases as well. For example, an initial dose of lactose may be about 0.6 to 1.0 gm, e.g., 0.8 gm, given in combination with about 10-15 mg, e.g., about 12.5 mg, of *L. acidophilus*. The dose of lactose may be increased incrementally by about 0.6 to 1.0 gm, e.g., 0.8 gm, and the accompanying dose of *L. acidophilus* may be increased by about 10-15 mg, e.g., about 12.5 mg, of *L. acidophilus*.

Fructooligosacharides (FOS), are a non-digestible, soluble-fiber that supports the growth of beneficial bacteria in the intestinal tract, particularly two important strains—*l. acidophilus* and *l. bifidus*. These two strains play an essential role in reducing the number of pathogenic bacteria. Additional nutritional properties, such as the effect on colonic pH and stool bulking justify their classification as dietary fibers. In experimental models, it has also been reported that they improve the bioavailability of essential minerals. As a fiber, it is thought to slow digestion and allow the painless reintroduction of lactose into the body. FOS are chain polymers of the sugar fructose that are found in a variety of foods. The sugar units can be linked in a single straight chain or can be a chain with side branches. In many cases small amounts of glucose are also contained in the chain. The length of the fructose chains can vary from source to source. Inulin is an example of a longer chained compound that is considered a FOS. The shorter (lower molecular weight) compounds tend to have a sweet taste. The size and complexity of the FOS molecule gives it desirable characteristics. Although the simple sugars fructose and glucose are quickly absorbed into the body by the intestines, FOS for the most part is indigestible and therefore acts as a non-digestible fiber in the diet. This is because the human does not have the enzymes to break down the FOS as it travels down the digestive tract. When the FOS reaches the large intestine and the colon, the bacteria that are found there start to break down the FOS. These bacteria have the enzymes needed to break down FOS. Bifido bacteria have been reported to use FOS. It is believed that foods that promote bifido bacteria growth are good for the health.

In some embodiments, FOS are given prior to beginning treatment with lactose. In some embodiments, FOS are given in conjunction with treatment with lactose, for part or all of the treatment with lactose. Thus, in some embodiments, some or all doses of lactose are accompanied by a dose of FOS. In some embodiments, FOS are given initially with the lactose, but then their use is discontinued. For example, the initial one, two, three, four, five, six, seven, eight, nine, ten, or more than ten days of treatment with lactose may include doses of FOS, with the use of FOS discontinued after that time. In some embodiments, FOS may be given for the first two days of treatment, then the administration of FOS is discontinued. In some embodiments, FOS, either alone or in combination with other substances or treatments are used after the treatment with lactose is terminated. The FOS may be taken for any suitable period after the termination of treatment with lactose, and may be taken daily or at regular or irregular intervals. Doses may be as described below.

Numerous FOS preparations are known in the art, and any suitable FOS preparation may be used in the methods and compositions of the invention. FOS may be used in a dose from about 1 mg to about 10 gm, or about 1 mg to about 5 gm, or about 2 mg to about 1000 mg, or about 2 mg to about 500 mg, or about 2 mg to about 200 mg, or about 2 mg to about 100 mg, or about 2 mg to about 50 mg, or about 2 mg to about 20 mg, or about 5 mg to about 10 mg, or about 5, 6, 7, 7.5, 8, 9, or 10 mg. In some embodiments, FOS are used in a dose of about 7.5 mg. The dose may be given in combination with lactose. In some embodiments, as lactose dose increases, the dose of FOS increases as well. For example, an initial dose of lactose may be about 0.6 to 1.0 gm, e.g., 0.8 gm, given in combination with about 5-10 mg, e.g., about 7.5 mg, of FOS. The dose of lactose may be increased incrementally by about 0.6 to 1.0 gm, e.g., 0.8 gm, and the accompanying dose of FOS may be increased by about 5-10 mg, e.g., about 7.5 mg, of FOS.

One or more buffers, optionally with a calcium counterion, may also be administered in methods of the invention. Any buffer suitable for consumption by the individual being treated, e.g., human, may be used. The buffer neutralizes stomach acidity which can, e.g., allow live bacteria to reach the gut. Buffers include citrates, phosphates, and the like. Some embodiments of the invention utilize a buffer with a calcium counterion, such as Calcium Phosphate Tribasic. The calcium can serve to restore the calcium that many lactose intolerant individuals are missing in their diet. A recent study demonstrated the ability of calcium phosphate to protect *lactobacillus acidophilus* from bile. It is an excellent buffering agent and will help neutralize stomach acidity.

In some embodiments, a buffer such as calcium phosphate is given prior to beginning treatment with lactose, e.g., in conjunction with administration of bacteria. In some embodiments, a buffer such as calcium phosphate is given in conjunction with treatment with lactose, for part or all of the treatment with lactose. Thus, in some embodiments, some or all doses of lactose are accompanied by a dose of a buffer such as calcium phosphate. In some embodiments, a buffer such as calcium phosphate is given initially with the lactose, but then its use is discontinued. For example, the initial one, two, three, four, five, six, seven, eight, nine, ten, or more than ten days of treatment with lactose may include doses of a buffer such as calcium phosphate, with the use of the discontinued after that time. In some embodiments, a buffer such as calcium phosphate may be given for the first two days of treatment, then the administration of buffer is discontinued. In some embodiments, a buffer such as calcium phosphate, either alone or in combination with other substances or treatments is used after the treatment with lactose is terminated. The a buffer such as calcium phosphate may be taken for any suitable period after the termination of treatment with lactose, and may be taken daily or at regular or irregular intervals. Doses may be as described below.

Numerous buffers suitable for human consumption are known in the art, and any suitable buffer may be used in the methods and compositions of the invention. Calcium triphosphate is an exemplary buffer and has the advantage that its counterion supplies a nutrient that is often lacking in lactose-intolerant individuals, i.e., calcium. The buffer may be used in a dose from about 2 to about 2000 mg, or about 4 to about 400 mg, or about 4 to about 200 mg, or about 4 to about 100 mg, or about 8 to about 50 mg, or about 10 to about 40 mg, or about 20 to about 30 mg, or about 20, 21, 22, 23, 24, 25, 26, 27, 28, 29, or 30 mg. In some embodiments, buffer is used in a dose of about 25 mg. In some embodiments, calcium phosphate is used in a dose of about 25 mg. The dose may be given in combination with lactose. In some embodiments, as lactose dose increases, the dose of buffer increases as well. For example, an initial dose of lactose may be about 0.6 to 1.0 gm, e.g., 0.8 gm, given in combination with about 20-30 mg, e.g., about 25 mg, of buffer, e.g., calcium phosphate. The dose of lactose may be increased incrementally by about 0.6 to 1.0 gm, e.g., 0.8 gm, and the accompanying dose of buffer, e.g., calcium phosphate, may be increased by about 20-30 mg, e.g., about 25 mg, of buffer, e.g., calcium phosphate.

In some embodiments, treatment with lactose, optionally in conjunction with bacteria, FOS, and/or buffer, is used in combination with other treatments to reduce the symptoms of lactose intolerance. Any suitable treatment for the reduction of symptoms of lactose intolerance may be used, e.g., the use of lactase. Lactase may be administered before, during, or after treatment with lactose, or any combination thereof. In some embodiments, especially when symptoms of lactose intolerance are not completely or substantially completely eliminated by lactose treatment, lactase is administered after lactose treatment is terminated. The lactase may be used on an as-needed basis.

In some embodiments, the treatment occurs in phases. One phase utilizes a single administration of lactose per day, generally though not necessarily with food, e.g., dinner. The dose of lactose increases over time. For example, the dose of lactose may increase each day. Another phase, generally following the first phase, utilizes two administrations of lactose per day, again, generally with food, e.g., with breakfast and dinner. Again, during this phase the dose of lactose increases over time, e.g., increasing each day. In some embodiments, the invention includes one phase in which lactose is administered once per day in conjunction with live bacteria. This phase, if used, is generally the first phase of the method. Alternatively, live bacteria may be administered during some or all of the entire period of treatment. For example, in some embodiments, live bacteria are included in a lactose-containing product that is administered to the individual. Typically, during the preceding phases no dairy products are consumed. A final phase of the protocol can involve the gradual reintroduction of dairy into the diet, either with or without the continuing use of the lactose-containing product used in the first phases of treatment. Finally, treatment is concluded and no further ingestion of lactose-containing product is required.

For example, in some embodiments, there are essentially five major phases to the regimen. The first phase relies upon the use of the lactose containing products administration for two days, along with live bacteria, e.g., yogurt containing live cultures. In the second phase, the lactose containing product is taken with food and typically a dinner for a period of about 10 to 30, or about 14 to 24, or about 16 to 20, or about 18 days. In the third phase, the lactose containing product is taken with both dinner and breakfast for another period of about 6 to 18, or about 8 to 16, or about 10 to 14, or about 12 days. For another 2, 3, 4, 5, or 6, e.g., about 4 days thereafter, the lactose containing product is administered with both dinner and breakfast, along with the addition of other diary products. Prior to this time, diary products are not consumed during the first phases, e.g., the first about 34 days of the regimen. This total period, e.g., of approximately 38 days, constitutes the full period in which the lactose containing product is consumed, but more importantly consumed essentially in these time periods. Following the actual administration of the lactose containing product, the regimen includes the actual ingestion of diary products for about at least every few days to maintain and build up the complete tolerance, but without the administration of the lactose containing product. In the first period of time, through the first, e.g., 18 days, the amount of the lactose containing product administered at dinner time increases regularly each day. Thereafter, and in the third period, the amount of the lactose containing product increases regularly each day in combination with a breakfast meal. Moreover, and for the final days, e.g., the final four days, a lactose containing food item, such as milk, also is regularly increased for those 4 days.

Thus, in one embodiment of the invention, a first dose of the lactose containing product is administered in increasing amounts for a 6-week period. On the first and second days of this period, promote bacteria, e.g., in a food containing product also having a live culture bacteria is administered with the lactose containing product. One such food item containing a live cultured bacteria is yogurt. Further, during the third phase during this 6-week period, a second dose of the lactose containing product is administered, typically at breakfast time. An example of the dosing regimen is shown in the following table:

TABLE I

| Week | Day | PM-Dosage | AM-Dosage |
| --- | --- | --- | --- |
| 1 | 1 | 1 tbs + 8 oz yogurt | |
| 1 | 2 | 1 tbs + 4 oz yogurt | |
| 1 | 3 | 1 tbs | |
| 1 | 4 | 2 tbs | |
| 1 | 5 | 3 tbs | |
| 1 | 6 | 4 tbs | |
| 1 | 7 | 5 tbs | |
| 2 | 8 | 6 tbs | |
| 2 | 9 | 7 tbs | |
| 2 | 10 | 8 tbs | |
| 2 | 11 | 9 tbs | |
| 2 | 12 | 10 tbs | |
| 2 | 13 | 11 tbs | |
| 2 | 14 | 12 tbs | |
| 3 | 15 | 13 tbs | |
| 3 | 16 | 14 tbs | |
| 3 | 17 | 15 tbs | |
| 3 | 18 | 16 tbs | |
| 3 | 19 | 16 tbs | 1 tbs |
| 3 | 20 | 16 tbs | 2 tbs |
| 3 | 21 | 16 tbs | 3 tbs |
| 4 | 22 | 16 tbs | 4 tbs |
| 4 | 23 | 16 tbs | 5 tbs |
| 4 | 24 | 16 tbs | 6 tbs |
| 4 | 25 | 16 tbs | 7 tbs |
| 4 | 26 | 16 tbs | 8 tbs |
| 4 | 27 | 16 tbs | 9 tbs |
| 4 | 28 | 16 tbs | 10 tbs |
| 5 | 29 | 16 tbs | 11 tbs |
| 5 | 30 | 16 tbs | 12 tbs |
| 5 | 31 | 16 tbs | 13 tbs |
| 5 | 32 | 16 tbs | 14 tbs |
| 5 | 33 | 16 tbs | 15 tbs |
| 5 | 34 | 16 tbs | 16 tbs |
| 5 | 35 | 9 oz milk | 9 oz milk |
| 6 | 36 | 10 oz milk | 10 oz milk |
| 6 | 37 | 11 oz milk | 11 oz milk |
| 6 | 38 | 12 oz milk | 12 oz milk |
| 6 | 39 | Cheese 1 oz | |
| 6 | 40 | Cheese 2 oz | |
| 6 | 41 | lactose tolerance achieved | |
| 6 | 42 | | |

In the first day of the regimen, the subject ingests 8 ounces of yogurt or other food product containing a live culture bacteria, along with 1 tablespoon of milk, at the dinner meal. As an example and considering the regimen shown in Table I, the subject will ingest 8 ounces of live culture bacterial yogurt on the first day, along with 1 tablespoon of milk with dinner. On the second day, the amount of the yogurt ingested is reduced to 4 ounces, although the administration of the milk remains the same. On the third day, administration of the yogurt is ceased, but the milk remains at 1 tablespoon. During the fourth through the 18th days, the amount of milk ingested with dinner is increased by 1 tablespoon each day until 16 tablespoons are reached on the day 18.

In the third phase of the regimen, and on, it can be seen that both 1 tablespoon of milk is ingested in the morning, with breakfast, and 16 tablespoons of milk are ingested with dinner. From day 16 until day 34, the same ratio of milk with dinner is maintained, but the morning dose increases daily at a rate of a tablespoon per day. In this way, by day 34, the subject is ingesting 32 tablespoons of milk.

It can also be seen that on day 35, ingestion of the lactose containing product is discontinued and in place thereof, milk is ingested, with 9 ounces of milk in the morning and an additional 9 ounces in the evening. The milk amounts are increased incrementally at a rate of an ounce per day, such that, by day 38, the subject is ingesting 12 ounces of milk with breakfast and an additional 12 ounces of milk at dinner.

Finally, on days 39 through 42, cheese is substituted for milk.

It will be recognized that Table I is only a single exemplary 6-week regimen. The actual days can vary, and the quantity of the dosages can similarly be modified according to each particular subject and the reactions encountered by that subject. Even though there may be variations in both the time period and the dosage rates, the concept of increasing the dosages of the lactose containing product for specific time periods is maintained and encompassed by the present invention.

As a simple example of variations in the above-identified regimen, it may be found that the subject is capable of ingesting more than 5 tablespoons of milk by day 7. As a result, the amount of milk ingested by day 7 may be increased to 6 tablespoons, etc. Determination of whether or not the subject is capable of increasing the dosage or the time period depends on whether or not the subject encounters any adverse affects. In the event that the subject does encounter adverse affects, the subject should resort back to the regimen as specified in Table I.

The same alterations can be made in the time intervals between the administration of the lactose containing product and the various other lactose containing food items. Thus, if desired, the subject could potentially alter the amount of the lactose food item every 12 hours. In like manner, that time period could vary to 36 or even 48 hours: As indicated previously, the lactose containing product of the invention may be administered as a pure powder lactose, the latter of which is mixed with water and consumed much in the same manner as a soft drink. The amount of the lactose can also be incorporated in one or more capsules, or otherwise, in the loose granular form, as indicated.

The table following Table II shows an example of a powder lactose regimen:

TABLE II

| Week | Day | PM-Dosage | AM-Dosage |
|---|---|---|---|
| 1 | 1 | s + 8 oz yogurt | |
| 1 | 2 | s + 4 oz yogurt | |
| 1 | 3 | s | |
| 1 | 4 | m | |
| 1 | 5 | m + s | |
| 1 | 6 | 2m | |
| 1 | 7 | 2m + s | |
| 2 | 8 | 3m | |
| 2 | 9 | 3m + s | |
| 2 | 10 | 4m | |
| 2 | 11 | 4m + s | |
| 2 | 12 | 5m | |

TABLE II-continued

| Week | Day | PM-Dosage | AM-Dosage |
|---|---|---|---|
| 2 | 13 | 5m + s | |
| 2 | 14 | 6m | |
| 3 | 15 | 6m + s | |
| 3 | 16 | 7m | |
| 3 | 17 | 7m + s | |
| 3 | 18 | 8m | |
| 3 | 19 | 8m | s |
| 3 | 20 | 8m | m |
| 3 | 21 | 8m | m + s |
| 4 | 22 | 8m | 2m |
| 4 | 23 | 8m | 2m + s |
| 4 | 24 | 8m | 3m |
| 4 | 25 | 8m | 3m + s |
| 4 | 26 | 8m | 4m |
| 4 | 27 | 8m | 4m + s |
| 4 | 28 | 8m | 5m |
| 5 | 29 | 8m | 5m + s |
| 5 | 30 | 8m | 6m |
| 5 | 31 | 8m | 6m + s |
| 5 | 32 | 8m | 7m |
| 5 | 33 | 8m | 7m + s |
| 5 | 34 | 8m | 8m |
| 5 | 35 | 9 oz milk | 9 oz milk |
| 6 | 36 | 10 oz milk | 10 oz milk |
| 6 | 37 | 11 oz milk | 11 oz milk |
| 6 | 38 | 12 oz milk | 12 oz milk |
| 6 | 39 | Cheese 1 oz | |
| 6 | 40 | Cheese 2 oz | |
| 6 | 41 | lactose tolerance achieved | |
| 6 | 42 | | |

In the foregoing Table II the designation "s" refers to a single zero sized capsule containing 0.8 gm of pure lactose powder, and this is equivalent to about 1 tablespoon of milk. The designation "m" refers to a double-sized zero capsule, which may be filled with 1.6 grams of lactose powder. The amount of the lactose ingested in any time interval, in accordance with Table II, is substantially identical to that regimen as shown in Table I. However, the form of the lactose is different.

In some protocols, lactose need not be administered with bacteria. Hence, the standard protocol starts with a subject taking 0.8 grams of lactose with a dinner. On days 2-16, the subject increases the dosage of lactose by 0.8 grams, thus they go from having 0.8 grams on day 1, to 1.6 grams on day 2, and 2.4 grams on day 3. On day 17, the subject starts the same process with breakfast, by taking 0.8 grams on day 17, then 1.6 grams on day 18 and so on. While this is going on, the subject continually takes 12.8 grams of lactose with dinner. Finally on day 33, the subject starts to re-introduce dairy products into their daily diet. While the dairy foods may vary, milk is the standard product a subject starts out with. Starting with drinking 6 ounces with breakfast and dinner, the subject gradually drinks 8 ounces, 10 ounces and 12 ounces of milk per day. At day 36, the subject has completed the protocol and may now enjoy dairy products pain-free. No future protocol, supplements or medication is needed for these subjects to consume dairy products.

An example of this dosing regimen is shown below in Table III.

TABLE III

| Week | Date | PM-lactose | AM-lactose | PM-Dairy | AM-Dairy |
|---|---|---|---|---|---|
| 1 | 1 | .8 grams | | | |
| 1 | 2 | 1.6 grams | | | |
| 1 | 3 | 2.4 grams | | | |

TABLE III-continued

| Week | Date | PM-lactose | AM-lactose | PM-Dairy | AM-Dairy |
|---|---|---|---|---|---|
| 1 | 4 | 3.2 grams | | | |
| 1 | 5 | 4 grams | | | |
| 1 | 6 | 4.8 grams | | | |
| 1 | 7 | 5.6 grams | | | |
| 2 | 8 | 6.4 grams | | | |
| 2 | 9 | 7.2 grams | | | |
| 2 | 10 | 8 grams | | | |
| 2 | 11 | 8.8 grams | | | |
| 2 | 12 | 9.6 grams | | | |
| 2 | 13 | 10.4 grams | | | |
| 2 | 14 | 11.2 grams | | | |
| 3 | 15 | 12 grams | | | |
| 3 | 16 | 12.8 grams | | | |
| 3 | 17 | 12.8 grams | .8 grams | | |
| 3 | 18 | 12.8 grams | 1.6 grams | | |
| 3 | 19 | 12.8 grams | 2.4 grams | | |
| 3 | 20 | 12.8 grams | 3.2 grams | | |
| 3 | 21 | 12.8 grams | 4 grams | | |
| 4 | 22 | 12.8 grams | 4.8 grams | | |
| 4 | 23 | 12.8 grams | 5.6 grams | | |
| 4 | 24 | 12.8 grams | 6.4 grams | | |
| 4 | 25 | 12.8 grams | 7.2 grams | | |
| 4 | 26 | 12.8 grams | 8 grams | | |
| 4 | 27 | 12.8 grams | 8.8 grams | | |
| 4 | 28 | 12.8 grams | 9.6 grams | | |
| 5 | 29 | 12.8 grams | 10.4 grams | | |
| 5 | 30 | 12.8 grams | 11.2 grams | | |
| 5 | 31 | 12.8 grams | 12 grams | | |
| 5 | 32 | 12.8 grams | 12.8 grams | | |
| 5 | 33 | | | 6 oz Milk | 6 oz Milk |
| 5 | 34 | | | 8 oz Milk | 8 oz Milk |
| 5 | 35 | | | 10 oz Milk | 10 oz Milk |
| 6 | 36 | | | 12 oz Milk | 12 oz Milk |

Although the doses shown here have been used and tested, variations in the doses and timing in which they are administered can still result in an effective treatment for increasing tolerance for lactose containing product. For example, the presented doses have been tested on adult subjects. Thus, when applying the protocol of the present invention to younger subjects, the weight of the subject might be a consideration. For example, a subject weighing 50 pounds may not require, and may not be capable of tolerating, the doses set forth in Table 1 at prescribed time in the protocol. As such, the dose administered to the subject may be proportionally scaled down based on his weight. Although the doses are disclosed as being administered with breakfast and dinner, alternatively the order of the doses may be switched, or may be administered at other times of the day with meals such as lunch or snacks (or conceivably with no meals). The program may also be reduced into a shortened or lengthened program. The program can work with an abbreviated 4 week program or it can be lengthened up to a 10 week program. Although the invention has been described for use in humans, it is also capable of being administered to other mammals.

Compositions

The invention also provides compositions for the treatment of the symptoms of lactose intolerance. The compositions contain lactose and one or more of: bacteria, FOS, and/or buffer. Additional ingredients include ingredients to improve handling, preservatives, flavorings and the like.

In some embodiments, the composition contains lactose and bacteria. The lactose will typically comprise more than 50% of the weight of the composition while the bacteria will typically comprise less than about 10%, 5%, 4%, 3%, or 2% of the compositions (all percentages are weight percent unless otherwise indicated). For example, lactose may be present at about 80-99.75% and the bacteria at about 0.25-2.10%, or the lactose may be present at about 89-94% and the bacteria at about 1.2-3.75%. In some embodiments, lactose is present at about 94.01% and bacteria, e.g., L. acidophilus, is present at about 1.47%. If the bacteria and lactose do not make up 100% of the composition, the remaining ingredients may be any suitable ingredients intended for the consumption of the individual, e.g., human, including, but not limited to, FOS and/or buffer, but also including ingredients intended to inhibit clumping and increase portability, such as silicone dioxide and microcyrstalline cellulose, or similar ingredients as are well-known in the art.

In some embodiments, the compositions contain lactose and FOS. For example, lactose may be present at about 80-99.75% and the FOS at about 0.10-1.89%, or the lactose may be present at about 89-94% and the FOS at about 0.40 to about 1.26%. In some embodiments, lactose is present at about 94.01% and FOS is present at about 0.88%. If the FOS and lactose do not make up 100% of the composition, the remaining ingredients may be any suitable ingredients intended for the consumption of the individual, e.g., human, including, but not limited to, bacteria and/or buffer, but also including ingredients intended to inhibit clumping and increase pourability, such as silicone dioxide and microcrystalline cellulose, or similar ingredients as are well-known in the art.

In some embodiments, the compositions contain lactose and buffer, e.g., calcium phosphate tribasic. For example, lactose may be present at about 80-99.75% and the buffer at about 0.50-4%, or the lactose may be present at about 89-94% and the buffer at about 1.2 to about 3.75%. In some embodiments, lactose is present at about 94.01% and buffer is present at about 2.94%. If the buffer and lactose do not make up 100% of the composition, the remaining ingredients may be any suitable ingredients intended for the consumption of the individual, e.g., human, including, but not limited to, bacteria and/or FOS, but also including ingredients intended to inhibit clumping and increase pourability, such as silicone dioxide and microcyrstalline cellulose, or similar ingredients as are well-known in the art.

In some embodiments, the compositions contain lactose, bacteria (e.g., *L. acidophilus*), and FOS. For example, lactose may be present at about 80-99.75%, bacteria at about 0.25-2.10%, and the FOS at about 0.10-1.89%, or the lactose may be present at about 89-94%, bacteria at about 0.91-1.95% and the FOS at about 0.40 to about 1.26%. In some embodiments, lactose is present at about 94.01%, bacteria at about 1.47%, and FOS is present at about 0.88%. If the bacteria, FOS and lactose do not make up 100% of the composition, the remaining ingredients may be any suitable ingredients intended for the consumption of the individual, e.g., human, including, but not limited to buffer, but also including ingredients intended to inhibit clumping and increase pourability, such as silicone dioxide and microcyrstalline cellulose, or similar ingredients as are well-known in the art.

In some embodiments, the compositions contain lactose, bacteria, and buffer. For example, lactose may be present at about 80-99.75%, bacteria at about 0.25-2.10%, and the buffer at about 0.50-4%, or the lactose may be present at about 89-94%, bacteria at about 0.91-1.95% and the buffer at about 1.2 to about 3.75%). In some embodiments, lactose is present at about 94.01%, bacteria at about 1.47%, and buffer is present at about 2.94%. If the bacteria, buffer and lactose do not make up 100% of the composition, the remaining ingredients may be any suitable ingredients intended for the consumption of the individual, e.g., human, including, but not limited to, FOS, but also including ingredients intended to inhibit clumping and increase pourability, such as silicone dioxide and microcyrstalline cellulose, or similar ingredients as are well-known in the art.

In some embodiments, the compositions contain lactose, FOS, and buffer. For example, lactose may be present at about 80-99.75%, FOS at about 0.10 to about 1.89%, and the buffer at about 0.50-4%, or the lactose may be present at about 89-94%, FOS at about 0.40 to about 1.26%, and the buffer at about 1.2 to about 3.75%. In some embodiments, lactose is present at about 94.01%, FOS at about 0.88%, and buffer is present at about 2.94%. If the FOS, buffer and lactose do not make up 100% of the composition, the remaining ingredients may be any suitable ingredients intended for the consumption of the individual, e.g., human, including, but not limited to, bacteria, but also including ingredients intended to inhibit clumping and increase pourability, such as silicone dioxide and microcyrstalline cellulose, or similar ingredients as are well-known in the art.

In some embodiments, the compositions contain lactose, bacteria, FOS, and buffer. For example, lactose may be present at about 80-99.75%, bacteria at about 0.25 to about 2.10%, FOS at about 0.10 to about 1.89%, and the buffer at about 0.50-4%, or the lactose may be present at about 89-94%, bacteria at about 0.91 to about 1.95%, FOS at about 0.40 to about 1.26%, and the buffer at about 1.2 to about 3.75%. In some embodiments, lactose is present at about 94.01%, bacteria at about 1.47%, FOS at about 0.88%, and buffer is present at about 2.94%. If the bacteria, FOS, buffer and lactose do not make up 100% of the composition, the remaining ingredients may be any suitable ingredients intended for the consumption of the individual, e.g., human, including, but not limited to, ingredients intended to inhibit clumping and increase pourability, such as silicone dioxide and microcyrstalline cellulose, or similar ingredients as are well-known in the art.

Additional ingredients include ingredients to improve handling, preservatives, flavorings and the like. In some embodiments, the compositions include microcrystalline cellulose and silicone dioxide.

In embodiments that include lactose, bacteria (e.g., *L. acidophilus*), buffer (e.g., calcium phosphate tribasic), microcrystalline cellulose and silicone dioxide, proportions and weights are as shown in the Table IV, below. As will be appreciated, weights are merely exemplary, and may be varied. For example, in some embodiments, the weight of lactose is 800 mg (0.8 g) and the other weights may be adjusted accordingly:

TABLE IV

| Ingredients | Weight | Percentage Range | Alternative Percentage Range | Exemplary Percentage |
|---|---|---|---|---|
| Lactose | 3,200.00 mg | 80-98.5 | 89-94 | 94.01 |
| Buffer, e.g., Calcium Phosphate Tribasic | 100.00 mg | 0.5-4.0 | 1.2-3.75 | 2.94 |
| Bacteria, e.g., *Lactobacillus Acidophilus* | 50.00 mg | 0.25-2.10 | 0.91-1.95 | 1.47 |
| Fructooligosacchrides (FOS) | 30.00 mg | 0.10-1.89 | 0.40-1.26 | 0.88 |
| Handling agent, e.g., Microcrystalline Cellulose | 20.00 mg | 0.95-1.15 | 0.18-0.92 | 0.59 |
| Handling agent, e.g., Silicon Dioxide | 4.00 mg | 0.04-0.32 | 0.08-0.19 | 0.12 |

Compositions of the invention include any suitable form, including liquid or powder. Powdered compositions may be as pure powder, or may be in the form of capsules, tablets, or the like. Powder may be packaged in bulk (e.g., in a container containing sufficient lactose and/or other substances for one individual to follow an entire course of treatment with increasing doses of lactose, or a portion of a course of treatment), or as individual packets (e.g., packets containing a single dose of lactose plus other components, or packets containing the dose of lactose and other components needed for a particular day of a lactose treatment regimen). If packaged in bulk, the powder may be in any suitable container. The container may also include one or more scoops or similar serving devices of a size or sizes appropriate to measure and serve one or more doses of lactose and, optionally, other ingredients included in the powder. Liquid compositions contain lactose and, optionally, other ingredients, in a suitable liquid, e.g., water or buffer. Liquid compositions may be provided in bulk (e.g., in a container containing sufficient lactose and/or other substances for one individual to follow an entire course of treatment with increasing doses of lactose, or a portion of a course of treatment), or as individual containers, such as cans, bottles, soft packs, and the like (e.g., containers containing a single dose of lactose plus other components in suitable liquid, or containers containing the dose of lactose and other components needed for a particular day of a lactose treatment regimen). The container may also include one or more measuring cups or similar serving devices of a size or sizes appropriate to measure and serve one or more doses of lactose and, optionally, other ingredients included in the liquid.

Kits

In a further aspect, the invention provides kits for the treatment of the symptoms of lactose intolerance. The kits include lactose in suitable packaging for use by an individual in the treatment of symptoms of lactose intolerance. Any of the compositions described herein may be packaged in the form of a kit. A kit may contain an amount of lactose and, optionally, other ingredients as described herein, sufficient for an entire course of treatment, or for a portion of a course of treatment. Thus, in some embodiments, a kit may include sufficient lactose for the first, second, third, fourth, fifth, and sixth weeks of treatment, or additional weeks of treatment if used, or any combination thereof. Doses of lactose may be individually packaged, or the lactose may be provided in bulk, or combinations thereof. Thus, in some embodiments, a kit provides, in suitable packaging, individual doses of lactose that correspond to dosing points in a treatment regimen, wherein the doses are packaged in one or more packages intended for use in the treatment of symptoms of lactose intolerance. For example, a kit may contain doses of lactose, as described herein, for a treatment program, where the lactose is taken in increasing doses, so that individual packets of lactose are increasing in amount of lactose contained in the packet, from lower doses intended for use at the start of the program to higher doses as the program progresses. As doses are provided for later points in the program, two or more doses per day may be provided, each in its individual packet. Each packet may be labeled to indicate the day and time of day that it is intended to be taken, or the packaging containing the packets may be so labeled, or both. A "packet," as used in this context, is any individual container that contains lactose, whether the lactose is in solid or liquid form, and can include a packet that contains powder, tablets, or pills, or a packet that contains a liquid.

In some embodiments, the lactose may be provided in bulk in a single container, or in two, three, four, five, or more than five containers (e.g., where each container contains enough lactose for a particular week of a treatment program). If more than one bulk container is provided, the bulk containers may be suitably packaged together to provide sufficient lactose for all or a portion of a treatment protocol. The container or containers can be labeled with a label indicating information useful to the individual performing the treatment protocol, such as dosing schedules.

The lactose may be packaged with other suitable substances, such as bacteria, FOS, and/or buffer, as described herein. The other substance or substances may be packaged separately from the lactose, or mixed with the lactose, or combinations thereof. Thus, in some embodiments, kits of the invention include a powder or liquid containing all the ingredients intended to be used in a course of treatment or a portion of a course of treatment, e.g., lactose and bacteria, FOS, and/or buffer. In some embodiments, lactose is packaged in one package or set of packages, and additional components, such as bacteria, FOS, and/or buffer, are packaged separately from the lactose.

Kits may further include written materials, such as instructions, expected results, testimonials, explanations, warnings, clinical data, information for health professionals, and the like. In some embodiments, the kits contain a label or other information indicating that the kit is only for use under the direction of a health professional, such as a dietician, nutritionist, nurse, physician, or other appropriate health professional. In some embodiments, the kits contain or include information, such as a label, designating the material within as a medical food.

In one embodiment, the invention provides a kit that includes a container of powder, where the powder includes lactose, and additionally FOS, bacteria, and/or buffer, and a label on the container that indicates proper dosage and schedule of use for the powder. The container may further include scoops or other measuring and/or serving devices. In one embodiment, the invention provides a kit that includes a container of liquid, where the liquid includes lactose, and additionally FOS, bacteria, and/or buffer, and a label on the container that indicates proper dosage and schedule of use for the liquid. The container may further include measuring and/or serving devices.

Business Methods

The invention also provides business methods for marketing compositions and methods for the treatment of the symptoms of lactose intolerance. In some embodiments, the invention provides a method of doing business that includes marketing a composition for the treatment of symptoms of lactose intolerance wherein the treatment is by administering increasing doses of lactose according to any of the methods described herein, optionally in combination with other substances such as FOS, bacteria, and buffers In some embodiments, the composition is part of a kit, as described herein. The methods may further include producing such compositions or kits. The marketing may be directly to the consumer, or to suitable health professionals, or combinations thereof. The methods of marketing used in these embodiments of the invention include, but are not limited to, print, television, or radio commercials, infomercials, internet advertising, testimonials, word of mouth, telemarketing, and the like.

EXAMPLES

Example 1

The standard regimen starts with each subject of a group taking 0.8 grams of lactose with dinner each evening. On days 2-16, the dosage of the lactose is increased by 0.8 grams, such that on day 2, the subject takes 1.6 grams, and on day 3, takes 2.4 grams. This process continues until day 16. On day 17, the subject starts the same process with breakfast by consuming 0.8 grams of the product on day 17 and 1.6 grams on day 18. This process continues elevating at the same rate. Simultaneously therewith, the subject is taking 12.8 grams of the lactose containing product with dinner.

On day 33, each subject starts a reintroduction of diary products into their daily diet. While the diary products may vary, milk is typically the standard product, at least as a starting point. When milk is used, the subject starts with 6 ounces with breakfast and dinner, and gradually increases to 8 ounces, 10 ounces, 12 ounces of milk per day. On day 36, the subject has completed the entire regimen and is able to consume dairy products thereafter with decreased lactose intolerant symptoms. An example of this dosing regimen is shown below in the Table.

| Week | Date | PM-lactose | AM-lactose | PM-Dairy | AM-Dairy |
|---|---|---|---|---|---|
| 1 | 1 | .8 grams | | | |
| 1 | 2 | 1.6 grams | | | |
| 1 | 3 | 2.4 grams | | | |
| 1 | 4 | 3.2 grams | | | |
| 1 | 5 | 4 grams | | | |
| 1 | 6 | 4.8 grams | | | |
| 1 | 7 | 5.6 grams | | | |
| 2 | 8 | 6.4 grams | | | |
| 2 | 9 | 7.2 grams | | | |
| 2 | 10 | 8 grams | | | |
| 2 | 11 | 8.8 grams | | | |
| 2 | 12 | 9.6 grams | | | |
| 2 | 13 | 10.4 grams | | | |
| 2 | 14 | 11.2 grams | | | |
| 3 | 15 | 12 grams | | | |
| 3 | 16 | 12.8 grams | | | |
| 3 | 17 | 12.8 grams | .8 grams | | |
| 3 | 18 | 12.8 grams | 1.6 grams | | |
| 3 | 19 | 12.8 grams | 2.4 grams | | |
| 3 | 20 | 12.8 grams | 3.2 grams | | |
| 3 | 21 | 12.8 grams | 4 grams | | |
| 4 | 22 | 12.8 grams | 4.8 grams | | |
| 4 | 23 | 12.8 grams | 5.6 grams | | |
| 4 | 24 | 12.8 grams | 6.4 grams | | |
| 4 | 25 | 12.8 grams | 7.2 grams | | |
| 4 | 26 | 12.8 grams | 8 grams | | |
| 4 | 27 | 12.8 grams | 8.8 grams | | |
| 4 | 28 | 12.8 grams | 9.6 grams | | |
| 5 | 29 | 12.8 grams | 10.4 grams | | |
| 5 | 30 | 12.8 grams | 11.2 grams | | |
| 5 | 31 | 12.8 grams | 12 grams | | |
| 5 | 32 | 12.8 grams | 12.8 grams | | |
| 5 | 33 | | | 6 oz Milk | 6 oz Milk |
| 5 | 34 | | | 8 oz Milk | 8 oz Milk |
| 5 | 35 | | | 10 oz Milk | 10 oz Milk |
| 6 | 36 | | | 12 oz Milk | 12 oz Milk |

It is again pointed out that the doses can be varied in the actual times of application. Thus, as a simple example, the regimen can be used with the subject starring out at a breakfast time and increasing the dosages on the 17th day at dinner time. Alternatively, other times of the day could be used. Moreover, the quantities can vary, depending on the physical conditions of the user. Thus, and particularly in the case of children, dosages can be reduced.

Example 2

A double-blind study of the ability of the lactose-based compositions and methods of the invention was made in order to determine reduction of the symptoms of lactose intolerance. More specifically, the study was conducted to determine whether graduated and controlled administration of lactose-containing product of the invention to subjects who have been confirmed as having lactose intolerance was effective in order to determine if the regimen of the invention was effective in relieving then lactose intolerant symptoms. For this purpose, a double-blind randomized study was conducted with the subjects following the 38-day regimen with a placebo, or otherwise, the lactose-containing product, itself.

Eight-six persons were pre-screened to determine lactose intolerance. Each of these subjects was between the ages of 18 and 55 and recruited from the Los Angeles area. A pre-Likert scale and a post-Likert scale was used to determine the severity of five particular symptoms of lactose intolerance. Each subject was recruited through advertisements posted in local newspapers in the greater Los Angeles area, as well as the worldwide web. Over 190 subjects were pre-screened for this study. Each subject rated symptoms of bloating, abdominal pain, cramps, diarrhea, and nausea. A ranked scale was used, with 1 indicating no symptoms, 2 indicating slight symptoms, 3 indicating mild symptoms, 4 indicating moderate symptoms, and 5 indicating severe symptoms. The maximum possible score was 20. A score of 14 or higher with no information suggesting milk allergy, irritable bowel symptoms, or pregnancies, allowed each subject to participate.

Each of the subjects were paired by age group and gender. Most members of each pair of subjects began the program within two days. One member of the pair randomly received a supply of the lactose-containing product, while the other received a placebo. This placebo was similar in appearance to the actual lactose-containing product. Detailed instructions for administration were given to each participant. In short, each subject was instructed to take the powdered formula, as well as the powdered placebo, and mix same with water for ingestion. Particular preparation dispensed to each subject was unknown both to the subject and the dispensing individual. A record of each was kept by a third party.

In conducting the study, the regimen described in Example 1 was used. Also, the lactose-containing product of the Table IV of ingredients in the Compositions section, above, was used and particularly that product identified as having the exemplary percentages. Each subject was contacted once a week for the first two weeks, and then each week thereafter, in order to check on their progress. Directions were provided on a personal basis if changes were needed. During the entire program, 5 extra days were included, and each subject was asked to follow this 42-day program until completion. On days 35-37, each subject consumed a measured amount of milk with breakfast and dinner. On day 38, the subjects were asked to incorporate at least 16 ounces of diary product into their diet for the next 5 days. Upon completion, each subject again rated their symptoms using the same Likert scale which was used in the pre-screening procedure. Subjects were again asked for another rating of symptoms after one month of completion of the program.

The data collected from the symptom score sheets was analyzed. Participants provided ratings for five symptoms of lactose intolerance on a 0 (no symptom) to 4 (severe symptom) sale. Data collection was successful. The total symptom scale provided scores ranging from 0 to 20, Data were collected pre-treatment for 73 individuals and 64 individuals (87.7%) completed the program and provided data at the conclusion of that program. Completion rates were 88.9% for those assigned to the group receiving the lactose product and 86.9% for those assigned to the placebo group. 61 individuals provided data between one and two months following completion of the program.

SUMMARY OF RESULTS

Data are summarized for all individuals that provided information for two or more data points (Table, below). At the pre-treatment measurement point, members of the two groups provided statistically equivalent ratings of their symptoms for lactose intolerance (t=0.95, n.s.)1. At the post-treatment measurement point, the group receiving the lactose-containing product provided symptom ratings that, in total, were 54.6 percent lower than their original ratings, while the placebo group ratings declined by 34.1 percent. At post-treatment, analyses (analysis of covariance employing the pre-treatment ratings as the covariate) indicated that the respondents receiving the lactose-containing produced reported a significant decline in symptoms relative to the placebo group (F=8.81, p>0.01). Approximately one month later, participants were contacted again. At that point, the individuals receiving the lactose-containing product provided symptom ratings that were 56.6 percent lower than then original ratings, while the placebo group ratings declined by only 23.3 percent. Again, these results were significantly different
(F=18.32, p>0.001):

TABLE V

|  | N | Pre-Treatment Mean (s.d.) | N | Post-Treatment Mean (s.d.) | N | 1-month follow-up Mean (s.d.) |
|---|---|---|---|---|---|---|
| Lactose | 32 | 14.1(2.6) | 32 | 3.7(5.6) | 29 | 3.3(5.8) |
| Placebo | 32 | 14.9(3.5) | 32 | 8.1(6.2) | 32 | 10.3(5.6) |

As well, the percentage of respondents with a decline of 10 or more points on the total ratings were examined. As would be expected, the results were similar. For the post-treatment measuring point, 71.9 percent of the Lactose group, but only 37.5 percent of the placebo group reported symptom declines of 10 points or greater on the rating scale ($\chi2=7.63$, p>0.01)$^2$. One month later, the observed differences had increased, and 79.3 percent of the Lactose group but only 18.8 percent of the placebo group reported a symptom rating scale decline of at least 10 points ($\chi2=22.37$, p>0.001).

Summary of Pairs with 3 Data Points (−26)

In this section, data are summarized for the 26 matched pairs of individuals that provided information for all 3 data points (Table below). At the pre-treatment measurement point, the two groups were statistically equivalent on their symptom rating scale totals (t=1.19, n.s.). At the post-treatment measurement point, the group receiving the lactose-containing product reported significantly lowered symptom severity relative to the placebo group (t=2.36, p>0.05). In addition, 73.1 percent of the group receiving the lactose-containing product versus 38.5 percent of the placebo group reported a symptom decline of at least 10 points on the rating scale, and this result was also statistically significant ($\chi2=6.33$, p>0.05). At the final measurement point, the group receiving the lactose-containing product provided symptom ratings that, in total, were 54.1 percent lower than their original ratings, while the placebo group ratings declined by only 26.3 percent. Analyses (a matched-pair t-test) indicated that the matched respondents receiving the lactose-containing product reported significantly lowered symptom severity relative to the placebo group (t=3.67, p>0.01). In addition, 76.9 percent of the group receiving the lactose-containing product versus 23.1 percent of the placebo group reported a symptom decline of at least 10 points on the rating scale, and this result was also statistically significant ($\chi2=15.08$, p>0.001).

The summary of the data for 3 data points is set forth in the Table below:

TABLE VI

|  | N | Pre-Treatment Mean (s.d.) | N | Post-Treatment Mean (s.d.) | N | 1-month follow-up Mean (s.d.) |
|---|---|---|---|---|---|---|
| Lactose | 26 | 13.8(2.5) | 26 | 3.9(6.0) | 26 | 3.7(6.1) |
| Placebo | 22 | 14.9(3.7) | 26 | 7.9(6.3) | 26 | 9.7(5.7) |

The present study confirmed the occurrence of decrease of symptoms when lactose intolerant subjects ingested a formulated lactose-containing product for 38 days and showed a decrease in the severity of all symptoms when they were challenged with a lactose load (8, 10, and 12 oz glass of milk) after metabolic adaptation compared with pre-adaption severity. Post one month data demonstrated the same degree of improved symptoms as subjects continued to incorporate dairy products into their diets.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes

What is claimed is:

1. A composition for ameliorating the symptoms associated with lactose intolerance, the composition comprising: a lactose reduced dairy product and an effective amount of a probiotic selected from the group consisting of the genus *Lactobacillus*, the genus *Bifidobacterium* and mixtures thereof, and a fiber, wherein the lactose reduced dairy product has reduced lactose content and is selected from the group consisting of a yogurt containing pre-digested lactose, an ice cream containing pre-digested lactose and a margarine containing pre-digested lactose; wherein the probiotic is present in an amount of from about 1 mg to about 1000 mg of the composition; and wherein the fiber comprises a fructo-oligosaccharide.

2. The composition of claim 1, wherein the fiber further comprises inulin.

3. The composition of claim 1, wherein the fiber is about 0.1 to about 1.26% of the composition.

4. The composition of claim 1, wherein the probiotic is present in an amount of about 2 mg to about 50 mg of the composition.

5. The composition of claim 1, wherein the probiotic is present in an amount of about 4 mg to about 25 mg of the composition.

6. The composition of claim 1, wherein the fiber is present in an amount of from about 1 mg to about 10 g of the composition.

7. The composition of claim 1, wherein said lactose reduced dairy product is the ice cream containing pre-digested lactose.

8. The composition of claim 1, wherein said lactose reduced dairy product is the yogurt containing pre-digested lactose.

9. The composition of claim 1, wherein said lactose reduced dairy product is the margarine containing pre-digested lactose.

10. The composition of claim 1 wherein the probiotic is a member of the genus *Lactobacillus*.

11. The composition of claim 1 wherein the probiotic is a member of the genus *Bifidobacterium*.

12. A method for treating lactose intolerance in a human subject in need thereof, the method comprising: administering a composition comprising a lactose reduced dairy product and an effective amount of a probiotic selected from the group consisting of the genus *Lactobacillus*, the genus *Bifidobacterium* and mixtures thereof, and a fiber wherein the lactose reduced dairy product has reduced lactose content and is selected from the group consisting of a yogurt containing pre-digested lactose, an ice cream containing pre-digested lactose, and a margarine containing pre-digested lactose; wherein the probiotic is present in an amount of from about 1 mg to about 1000 mg of the composition; and wherein the fiber comprises a fructo-oligosaccharide.

13. The method of claim 12, wherein said lactose reduced dairy product is the ice cream containing pre-digested lactose.

14. The method of claim 12, wherein said lactose reduced dairy product is the yogurt containing pre-digested lactose.

15. The method of claim 12, wherein said lactose reduced dairy product is the margarine containing pre-digested lactose.

* * * * *